United States Patent
Greenberg et al.

(10) Patent No.: US 9,149,176 B2
(45) Date of Patent: Oct. 6, 2015

(54) 4-WAY CYSTOSCOPY CATHETER

(71) Applicant: EMMY MEDICAL, LLC, Holliston, MA (US)

(72) Inventors: James Adam Greenberg, Weston, MA (US); Ronald D. Adams, Holliston, MA (US); Neeraj Kohli, Natick, MA (US); David Harari, San Diego, CA (US)

(73) Assignee: EMMY MEDICAL, LLC, Holliston, MA (US)

( * ) Notice: Subject to any disclaimer, the term of this patent is extended or adjusted under 35 U.S.C. 154(b) by 0 days.

(21) Appl. No.: 14/542,220

(22) Filed: Nov. 14, 2014

(65) Prior Publication Data

US 2015/0065807 A1   Mar. 5, 2015

Related U.S. Application Data

(63) Continuation-in-part of application No. PCT/US2013/059822, filed on Sep. 13, 2013.

(60) Provisional application No. 61/700,841, filed on Sep. 13, 2012, provisional application No. 61/977,001, filed on Apr. 8, 2014, provisional application No. 62/009,848, filed on Jun. 9, 2014.

(51) Int. Cl.
*A01B 1/00* (2006.01)
*A61M 25/00* (2006.01)
(Continued)

(52) U.S. Cl.
CPC ............. *A61B 1/307* (2013.01); *A61B 1/00135* (2013.01); *A61B 1/00154* (2013.01);
(Continued)

(58) Field of Classification Search
CPC ................ A61M 25/0017; A61M 2025/0004; A61M 25/04; A61M 2025/0681; A61M 2025/1061; A61M 2210/1085; A61M 2210/166; A61B 1/307
See application file for complete search history.

(56) References Cited

U.S. PATENT DOCUMENTS

| 4,148,319 A | 4/1979 | Kasper et al. |
| 4,445,892 A | 5/1984 | Hussein et al. |

(Continued)

FOREIGN PATENT DOCUMENTS

| EP | 0402467 | 12/1990 |
| EP | 0609386 | 8/1994 |
| EP | 2163215 | 3/2010 |

OTHER PUBLICATIONS

Suru International Pvt. Ltd., Foley Baloon Catheter, http://www.suru.com/fole.htm, retrieved by Applicant on Jan. 28, 2014, Publication Date Unknown.

(Continued)

*Primary Examiner* — Kevin C Sirmons
*Assistant Examiner* — William Carpenter
(74) *Attorney, Agent, or Firm* — Knobbe Martens Olson & Bear LLP

(57) ABSTRACT

Systems and methods of cannulating a body orifice such as a bladder are disclosed. A cystoscopy catheter can include a proximal end, a distal end having at least one exit port, and a flexible elongate tubular body therebetween; an inflatable balloon near the distal end of the catheter, the balloon transformable from an unexpanded and an expanded configuration; a first proximal port for fluid inflow; a second proximal port for fluid outflow; a third proximal port for balloon inflation, in fluid connection with the balloon; and a fourth proximal port for insertion of a diagnostic and/or therapeutic instrument such as a cystoscope therethrough, wherein the first, second, and fourth proximal ports are fluidly connected to a common central lumen extending through the elongate tubular body to the exit port on the distal end.

20 Claims, 18 Drawing Sheets

(51) Int. Cl.
  *A61B 1/307* (2006.01)
  *A61M 25/04* (2006.01)
  *A61B 1/00* (2006.01)
  *A61B 1/015* (2006.01)
  *A61B 1/05* (2006.01)
  *A61M 25/10* (2013.01)

(52) U.S. Cl.
  CPC . *A61B1/015* (2013.01); *A61B 1/05* (2013.01); *A61M 25/04* (2013.01); *A61M 25/0017* (2013.01); *A61M 25/1002* (2013.01)

(56) References Cited

U.S. PATENT DOCUMENTS

| | | | |
|---|---|---|---|
| 4,470,407 A | | 9/1984 | Hussein |
| 4,576,145 A | | 3/1986 | Tsuno et al. |
| 4,685,449 A | | 8/1987 | Bonnet |
| 4,779,611 A | | 10/1988 | Grooters et al. |
| 5,041,093 A | | 8/1991 | Chu |
| 5,152,277 A | | 10/1992 | Honda et al. |
| 5,188,596 A | * | 2/1993 | Condon et al. ............ 604/103.1 |
| 5,209,725 A | * | 5/1993 | Roth ........................... 604/508 |
| 5,246,421 A | * | 9/1993 | Saab ........................... 606/194 |
| 5,287,845 A | * | 2/1994 | Faul et al. .................... 600/135 |
| 5,308,325 A | | 5/1994 | Quinn et al. |
| 5,320,091 A | * | 6/1994 | Grossi et al. ................. 600/104 |
| 5,437,673 A | * | 8/1995 | Baust et al. .................... 606/23 |
| 5,456,673 A | * | 10/1995 | Ziegler et al. ................ 604/264 |
| 5,624,395 A | * | 4/1997 | Mikhail et al. ............. 604/99.04 |
| 5,693,001 A | * | 12/1997 | Salama ........................... 600/29 |
| 5,810,790 A | | 9/1998 | Ebling et al. |
| 5,868,708 A | | 2/1999 | Hart et al. |
| 6,254,570 B1 | * | 7/2001 | Rutner et al. ............ 604/101.02 |
| 6,422,997 B1 | | 7/2002 | Green et al. |
| 6,569,150 B2 | | 5/2003 | Teague et al. |
| 6,689,148 B2 | | 2/2004 | Sawhney et al. |
| 6,871,740 B1 | * | 3/2005 | Cao .............................. 206/364 |
| 7,063,679 B2 | | 6/2006 | Maguire et al. |
| 7,922,650 B2 | | 4/2011 | McWeeney et al. |
| 8,083,670 B2 | | 12/2011 | Ikeda |
| 8,114,113 B2 | | 2/2012 | Becker |
| 8,177,741 B2 | | 5/2012 | Hammack et al. |
| 8,206,347 B2 | | 6/2012 | Burnside et al. |
| 2002/0165521 A1 | * | 11/2002 | Cioanta et al. ................ 604/509 |
| 2003/0055470 A1 | * | 3/2003 | Mon et al. ..................... 607/101 |
| 2003/0149468 A1 | | 8/2003 | Wallsten ...................... 623/1.11 |
| 2003/0153899 A1 | * | 8/2003 | Eshel et al. ................... 604/544 |
| 2004/0073159 A1 | * | 4/2004 | Nelson ............................ 604/21 |
| 2006/0004323 A1 | | 1/2006 | Chang et al. |
| 2006/0252993 A1 | | 11/2006 | Freed et al. |
| 2006/0293560 A1 | * | 12/2006 | Nguyen et al. ................ 600/104 |
| 2007/0282168 A1 | * | 12/2007 | Kaye et al. .................... 600/159 |
| 2009/0005741 A1 | | 1/2009 | Martin et al. |
| 2009/0024089 A1 | * | 1/2009 | Levine et al. ................. 604/104 |
| 2009/0030370 A1 | * | 1/2009 | Nishtala et al. .......... 604/103.01 |
| 2009/0318757 A1 | | 12/2009 | Singh |
| 2013/0012778 A1 | | 1/2013 | Bayer et al. |
| 2013/0060211 A1 | | 3/2013 | Adams, Jr. |

OTHER PUBLICATIONS

PCT Search Report and Written Opinion of the International Searching Authority dated Dec. 26, 2013, in 9 pages, regarding International Application No. PCT/US2013/059822.

* cited by examiner

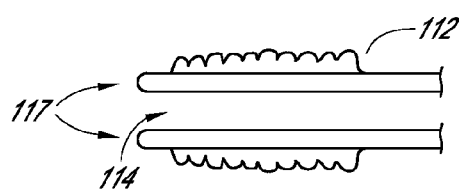
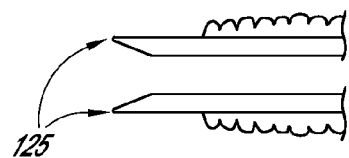
FIG. 7A   FIG. 7D
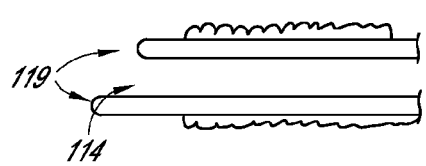
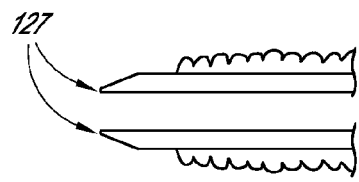
FIG. 7B   FIG. 7E
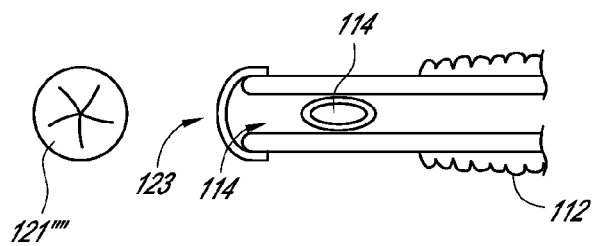
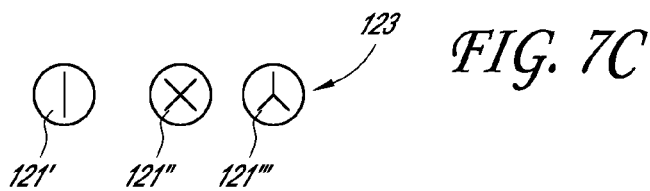
FIG. 7C

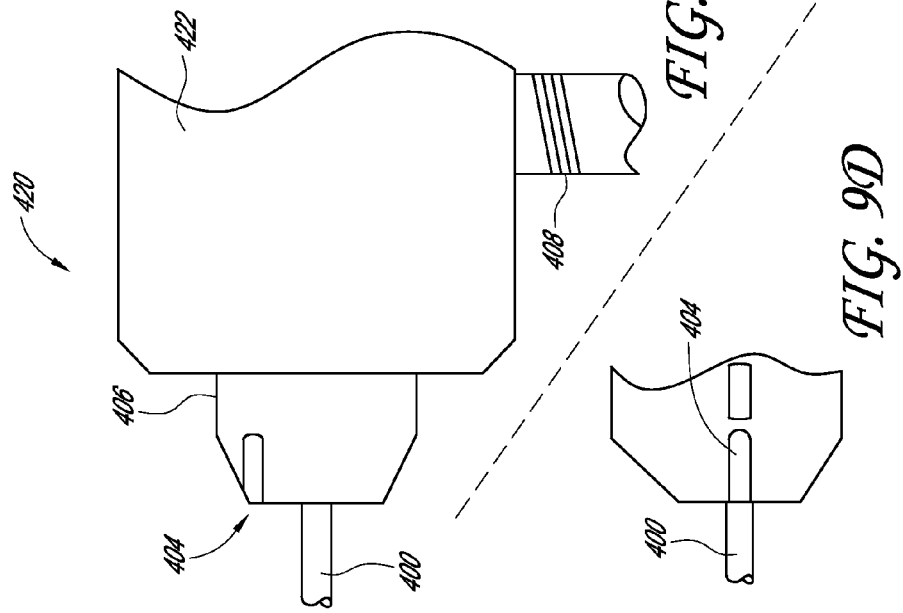
FIG. 9C
FIG. 9D
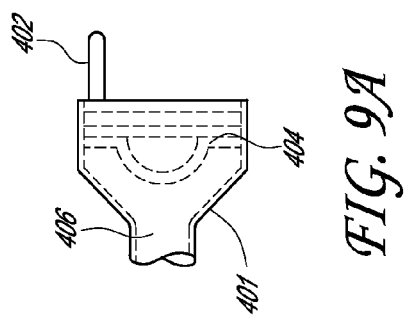
FIG. 9A
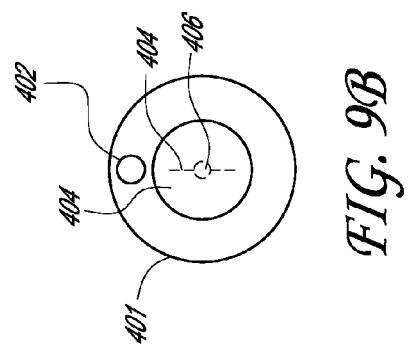
FIG. 9B

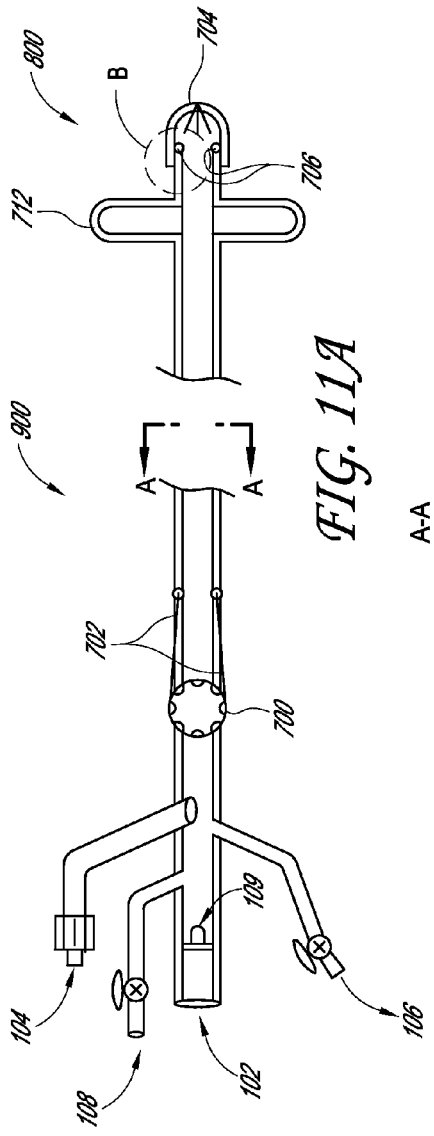
FIG. 11A
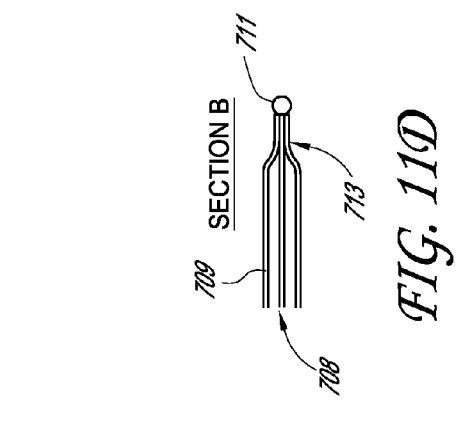
FIG. 11B
FIG. 11D
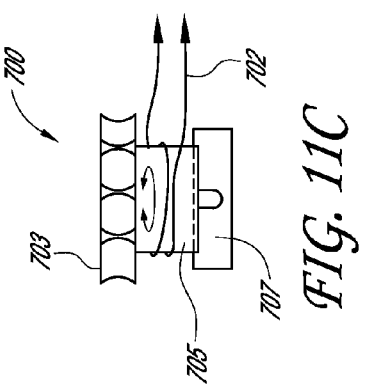
FIG. 11C

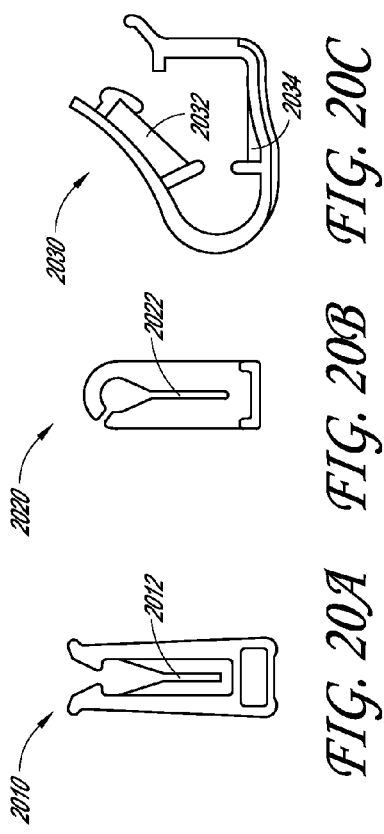
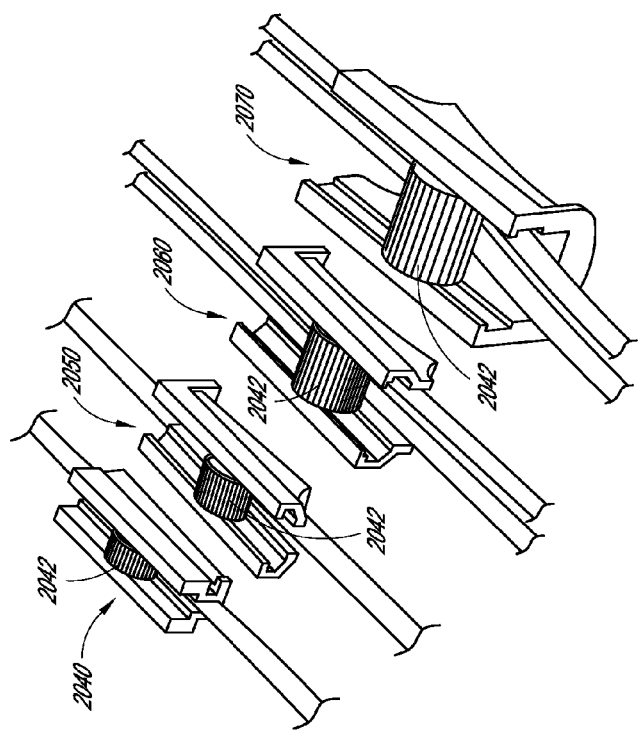
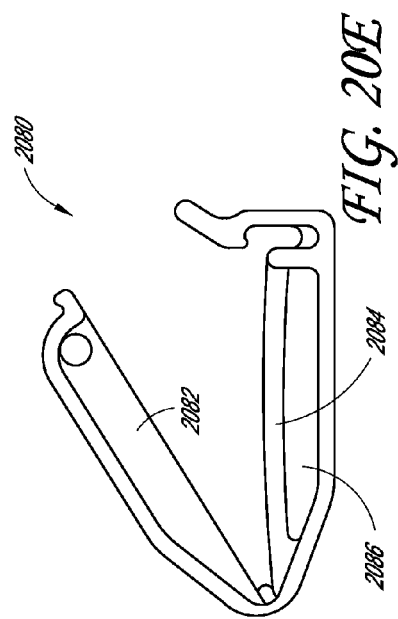
FIG. 20A  FIG. 20B  FIG. 20C  FIG. 20D  FIG. 20E

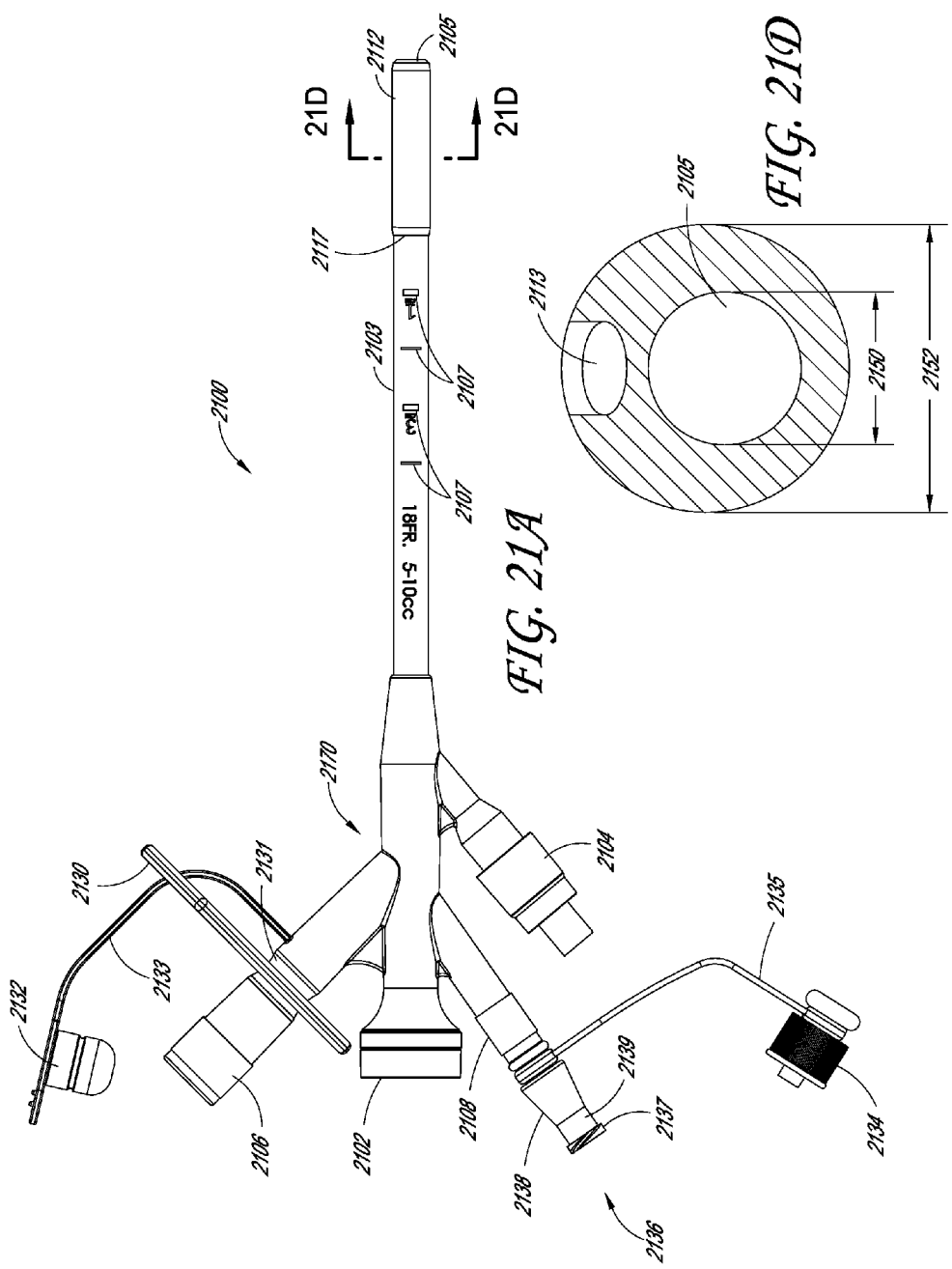

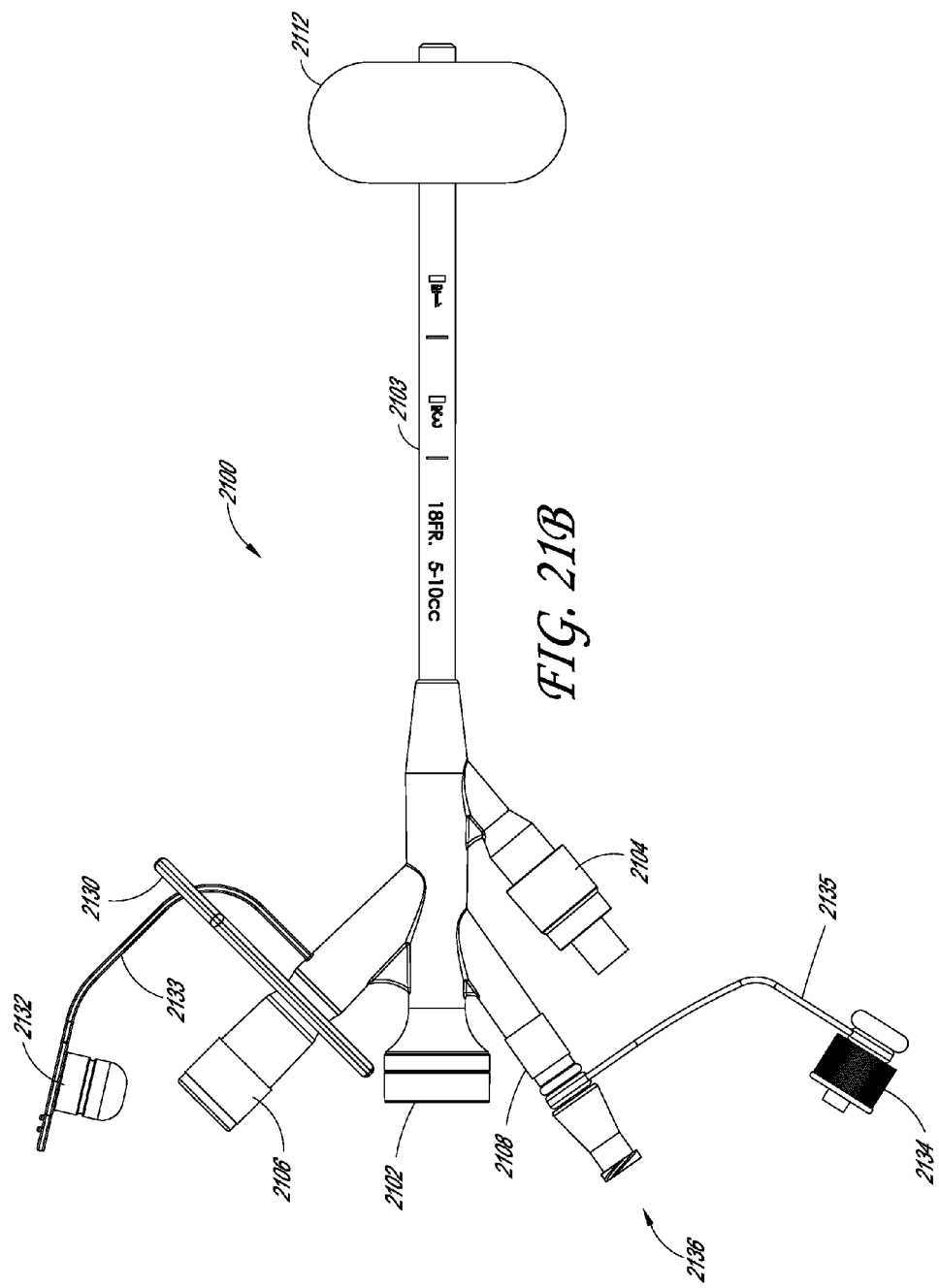

4-WAY CYSTOSCOPY CATHETER

CROSS-REFERENCE TO RELATED APPLICATIONS

This application is a continuation-in-part of PCT Application No. PCT/US2013/059822, titled 4-WAY CYSTOSCOPY CATHETER WITH LOW-PROFILE BALLOON, filed Sep. 13, 2013, which claims the benefit of U.S. Provisional Patent Application No. 61/700,841, filed Sep. 13, 2012. This application also claims the benefit of U.S. Provisional Patent Application No. 61/977,001, titled URINARY ACCESS CATHETER SYSTEM FOR CYSTOSCOPY, filed Apr. 8, 2014, and U.S. Provisional Patent Application No. 62/009,848, titled 4-WAY URINARY ACCESS CATHETER, filed Jun. 9, 2014. Each of the foregoing applications is hereby incorporated by reference herein in its entirety.

BACKGROUND

1. Field

This disclosure relates generally to the field of catheters for draining the urinary bladder.

2. Description

A urinary bladder tube is used in certain patients who have undergone major surgery, or any patient who is unable to urinate. There are many causes for inability to urinate. These causes differ with age and sex. For example, a small child may not urinate because of some congenital abnormality obstructing the bladder neck or urethra. In females, inability to urinate occurs in neurological diseases, after delivery of a baby, or after major abdominal or pelvic surgery. In a male, the most common causes of inability to urinate are an obstructing prostate, neurological diseases, or after major abdominal or pelvic surgery.

It can be desirable to continuously drain the bladder after major surgery at least for the purpose of monitoring the hourly urine output. It is also desirable to continuously drain the bladder by an indwelling Foley catheter in medical conditions where the measurement of hourly urine output is important to the well-being of the patient.

It can also be desirable to drain the bladder by an indwelling catheter after prostate or bladder surgery. Diverting the urine and blood will promote fast healing and prevent clots from building up in the bladder, which often cause more bleeding and severe pain.

It can also be important to drain the bladder by an indwelling catheter for pelvic surgeries. By draining the bladder, the operating space in the pelvis can be increased and it can facilitate access to structures such as the uterus in female patients.

It is also recognized that it can be recommended in clinical practice after pelvic surgeries to conduct an assessment of the bladder and ureters to ensure that no damage to these organs has occurred. In many cases an optimal way for making this assessment is the use of a cystoscope where the internal surface of the bladder can be viewed as well as the vesicoureteral junction. The vesicoureteral junction can be observed to look for flow of urine into the bladder indicating that no impairment of the ureters, bladder, or other structures has occurred during the surgery. In some cases, use of an intravenous dye such as indigo carmine can be used to visualize urinary tract flow and determine possible leakage. In the U.S. today, there are over 1 million gynecologic pelvic procedures performed each year. The incidence of urologic injury has been reported to range from 1 to 3%. During laparoscopic hysterectomy, the incidence of ureteral injury has been reported at 0.2 to 4.3%. Reoperation, when necessary if an undetected injury has occurred, carries an average expense of $8,000-$12,000. Today, many surgeons defer the urologic assessment due to costs, risks, inconvenience and the additional time required.

Currently, cystoscopy is performed through a 3 piece rigid metal system which needs assembly and availability of reusable sterilized equipment in the operating room. The procedure has remained largely unchanged for over 3 decades. The system is cumbersome, complicated, expensive, and not always available. In addition, it requires increased time of catheter removal and cystoscope assembly as well as multiple instances of urethral instrumentation, increasing risk of infection and urethral trauma. Systems and methods as disclosed herein can obviate these shortcomings.

In certain bladder or prostate surgeries, continuous bladder irrigation is used. This is achieved by introducing fluid continuously into the bladder and simultaneously draining the bladder. This type of Foley catheter is called a three-way catheter. One port will serve as fluid irrigation port into the bladder. The second port is for continuous drainage of the bladder contents into a large urine bag. The third port is for a valve mechanism where a balloon is inflated inside the bladder to keep the tip of the Foley catheter indwelling inside the bladder.

In certain patients, the bladder must be drained for many years, such as debilitated patients or those with neurological or spinal cord lesions. If the bladder is not drained, the pressure in the bladder will build up and the kidneys will be obstructed. Continuous bilateral kidney obstruction may lead to renal failure.

Therefore, the use of an indwelling catheter can be clinically advantageous, and could be life-saving, both in an acute and chronic long term settings. Some examples of Foley catheters are disclosed, for example, in U.S. Pat. No. 5,810,790 to Ebling et al. and U.S. Pat. No. 6,096,013 to Hakky et al., which are hereby incorporated by reference herein in their entireties.

SUMMARY

In some embodiments, disclosed herein is a 4-Way indwelling catheter. The catheter can function as a traditional Foley catheter at the start of a procedure in which the bladder is drained to provide optimum access and visualization of the pelvis. At the point in the procedure when the intra-procedure cystoscopy is to be performed, the 4-Way Foley catheter eliminates the need to remove the original Foley catheter. The 4-Way Foley can include a balloon and inflation channel to stabilize the catheter in the bladder; a central lumen with a one way valve to enable the insertion of a cystoscope; an inflow port with a control valve; and an outflow port with a control valve to enable bladder drainage. In some embodiments, the elongate body of the catheter distally beyond the proximal ports is limited to no more than, or exactly two lumens—the balloon inflation lumen and the central fluid/drainage/instrument lumen.

Disclosed herein is a cystoscopy catheter, comprising a proximal end, a distal end having at least one exit port, and a flexible elongate tubular body therebetween; an inflatable balloon near the distal end of the catheter, the balloon transformable from an unexpanded and an expanded configuration; a first proximal port for fluid inflow; a second proximal port for fluid outflow; a third proximal port for balloon inflation, in fluid connection with the balloon; and a fourth proximal port for insertion of a cystoscope or other diagnostic and/or therapeutic instrument therethrough, the port having a sealing structure therein, wherein the first, second, and fourth proximal ports are fluidly connected to a common central lumen extending through the elongate tubular body to the exit port on the distal end.

In some embodiments, the first proximal port comprises a multifunction connector, the multifunction connector comprising a threaded portion, a tapered portion, and an annular region therebetween, wherein the annular region comprises a smaller outer diameter than the threaded portion. In some embodiments, the catheter further comprises a tethered cap comprising threads to couple with the threaded portion of the multifunction connector. In some embodiments, the catheter further comprises a tethered cap configured to seal the second proximal port. In some embodiments, the tethered cap is integrally molded to the catheter. In some embodiments, the catheter further comprises a clamp that provides an alternative method of sealing the second proximal port, the clamp configured to pinch a section of tubing to limit fluid communication between the second proximal port and the common central lumen. In some embodiments, the catheter further comprises a tapered portion extending about the fourth proximal port. In some embodiments, the elongate tubular body comprises a plurality of markings regularly-spaced in an axial direction. In some embodiments, the balloon has a spherical expanded shape. In some embodiments, the balloon has an oblong expanded shape. In some embodiments, a distal tip of the distal end extends in an axial direction no more than 1 millimeter beyond a distal end of the balloon in its expanded configuration. In some embodiments, a distal tip of the distal end extends in an axial direction no more than 5 millimeters beyond a distal end of the balloon in its expanded configuration. In some embodiments, a distal tip of the distal end extends in an axial direction no more than 10 millimeters beyond a distal end of the balloon in its expanded configuration. In some embodiments, an expanded axial length of the balloon is no greater than about 25 millimeters. In some embodiments, the balloon in its expanded configuration has a radial dimension that is at least about 1.5× of its axial dimension. In some embodiments, the balloon in its expanded configuration has a radial dimension that is at least about 2× of its axial dimension. In some embodiments, the balloon in its expanded configuration has a radial dimension that is at least about 4× of its axial dimension. In some embodiments, the balloon in its expanded configuration has a radial dimension that is at least about 5× of its axial dimension. In some embodiments, the balloon in its expanded configuration has a volume of no more than about 5 cc. In some embodiments, the balloon in its expanded configuration has a volume of no more than about 3 cc. In some embodiments, the distal end comprises a rounded distal tip. In some embodiments, the distal end comprises a beveled distal tip. In some embodiments, the distal end comprises an end cap having a slot therein. In some embodiments, the distal end comprises at least two distal ports, wherein at least one distal port is positioned on a distal surface of the distal end and at least one distal port is positioned on a side surface of the distal end. In some embodiments, the distal end is movable from a first configuration coaxial with a longitudinal axis of the elongate tubular body to a second configuration not coaxial with the longitudinal axis of the elongate tubular body. In some embodiments, the second configuration comprises a curved state. In some embodiments, the catheter further comprises a deflection control on the elongate tubular body. In some embodiments, the deflection control comprises a rotatable knob. In some embodiments, the catheter further comprises at least one pullwire operably connected proximally to the deflection control and operably connected distally to the distal end of the catheter.

In some embodiments, disclosed herein is a cystoscopy catheter, comprising: a proximal end, a distal end having at least one exit port, and a flexible elongate tubular body therebetween; an inflatable balloon near the distal end of the catheter, the balloon transformable from an unexpanded and an expanded configuration; a first proximal port for at least one of fluid inflow or outflow; a second proximal port for balloon inflation, in fluid connection with the balloon; and a third proximal port for insertion of a cystoscope or other diagnostic and/or therapeutic instrument therethrough, wherein the first and third proximal ports are fluidly connected to a common central lumen extending through the elongate tubular body to the exit port on the distal end, wherein the balloon in its expanded configuration has a radial dimension that is at least about 1.5× of its axial dimension.

Also disclosed herein is an indwelling bladder catheter, comprising: a proximal end, a distal end having at least one exit port, and a flexible elongate tubular body therebetween; an inflatable balloon near the distal end of the catheter, the balloon transformable from an unexpanded and an expanded configuration; a first proximal port for at least one of fluid inflow or outflow; a second proximal port for balloon inflation, in fluid connection with the balloon; wherein the first proximal port is fluidly connected to a common central lumen extending through the elongate tubular body to the exit port on the distal end, wherein the balloon in its expanded configuration has a radial dimension that is at least about 1.5× of its axial dimension.

In some embodiments, disclosed herein is a method of performing a urologic or gynecologic procedure such as cystoscopy, comprising cannulating the urethra with a catheter, the catheter comprising: a proximal end, a distal end having at least one exit port, and a flexible elongate tubular body therebetween; an inflatable balloon near the distal end of the catheter, wherein the balloon in its expanded configuration has a radial dimension that is at least about 1.5× of its axial dimension; advancing the catheter distally into the bladder; flowing media into a balloon proximate the distal end of the catheter such that the balloon when expanded has a radial dimension that is at least about 1.5× of its axial dimension; and advancing an instrument, such as a cystoscope, through a proximal port of the catheter, through the flexible elongate tubular body, and through the exit port of the catheter. In some embodiments, the method further comprises deflecting the distal end of the catheter. In some embodiments, deflecting the distal end of the catheter comprises actuating a deflection control on the flexible elongate tubular body.

BRIEF DESCRIPTION OF THE DRAWINGS

FIGS. 7A-7E illustrate various embodiments of distal tip catheter configurations.

FIGS. 9A-9D illustrates an embodiment of a keyed catheter scope port and its attachment to an endoscope, such as a cystoscope.

FIGS. 11A-11D and 12 illustrate an indwelling catheter that can be steerable and curvable via a deflectable distal end, according to some embodiments.

FIGS. 20A through 20E illustrate embodiments of tubing sealing devices.

FIGS. 21A through 21D illustrate another embodiment of a urinary access catheter.

DETAILED DESCRIPTION

Cystoscopy involves passing a visualization device such as a fiber optic or rod lens scope into the bladder. The procedure is often conducted in conjunction with an operative procedure that includes the installation of a urinary catheter to first drain the bladder to make space in the abdominal cavity. Once the bladder has been drained, it can be flushed to remove any residual materials. The urinary catheter is then withdrawn and a visualization device is passed into the bladder. In some procedures, the visualization device needs to be rotated to identify the ureteral orifices to check for patency of the ureters and normality of the bladder lining. Placement of the viewing device is typically done as an independent insertion of the viewing instrument where the drainage catheter must be removed prior to the insertion of the viewing instrument. It is recognized that each insertion of a new device creates an additional risk for urethral and bladder damage plus the potential for a urinary tract infection. Thus, there is therefore a need for a device or system to both provide urinary access and drainage and the ability to visualize the bladder that minimizes the number of insertions.

The present disclosure describes various embodiments of methods, systems, and devices that enable a catheter to function as a traditional Foley catheter for portions of a procedure in which the bladder is irrigated and/or drained. The catheter can also, however, enable post-procedure cystoscopy to be performed without removing the catheter. In some embodiments, a novel urinary access system is described that provides a means for a single insertion of an access catheter that can offer both drainage and inflow capabilities, as well as bladder visualization.

Figure 1:
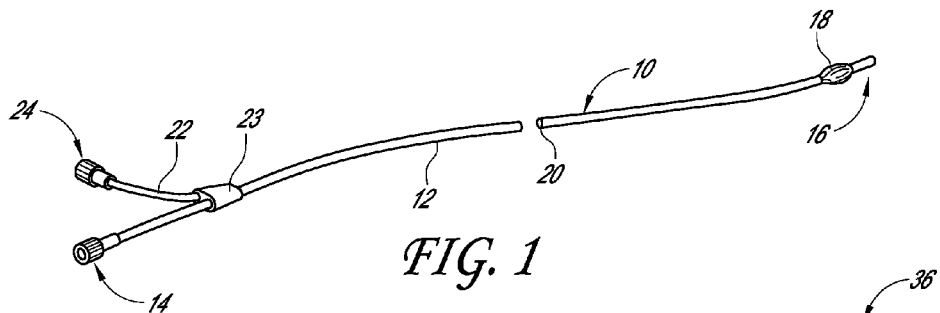
FIG. 1 is a side elevation view of a balloon-retained catheter, according to some embodiments.

Referring to FIG. 1, a balloon-retained catheter 10, here being a Foley catheter, is shown. The catheter 10 includes a length of tubing 12 having a first proximal port 14 and an open distal end 16, with the distal opening including laterally and/or distally disposed apertures. Immediately behind the distal end 16 is an expandable member, e.g., an inflatable balloon 18 surrounding a portion of the tubing 12. A central lumen 20 defined by the tubing 12 extends from at least the hub 23 proximally to the distal end 16 thereof for conveying fluid therethrough. A second lumen 22 is disposed within the tubing 12 and is accessible via a second proximal port 24. The second lumen 22 leads to the interior of the balloon 18 for passage of fluid for balloon inflation and deflation. In some embodiments (not shown), a catheter may be in the form of a 3-way catheter and can include a third proximal port which can be used for continuous bladder irrigation, for example, in communication with a central lumen 20 distally past the proximal hub 23.

Figure 2:
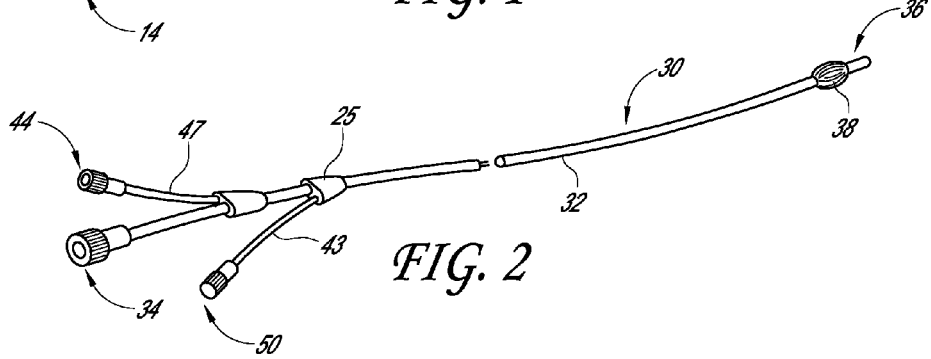
FIG. 2 is a side elevation view of a balloon-retained catheter having a lumen for accommodating an endoscope, according to some embodiments.
Figure 3:
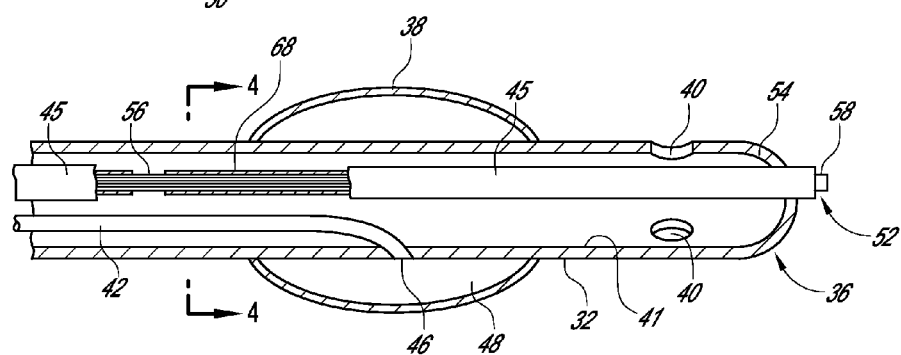
FIG. 3 is an enlarged cross sectional view of the distal portion of the catheter as shown in FIG. 2, according to some embodiments.
Figure 4:
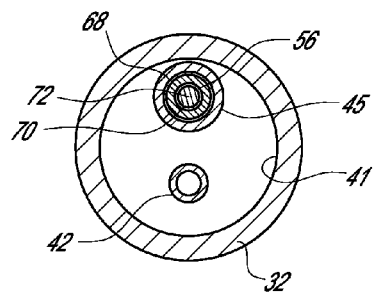
FIG. 4 is a cross sectional view taken along line 4-4 of FIG. 3.

Referring now to FIGS. 2 through 4, a balloon-retained catheter 30 is shown wherein an instrument, e.g., an endoscope can be retained. The catheter 30 can be identical or similar to the catheter 10 of FIG. 1, except with the capability of housing an endoscope as hereafter described. The catheter 30 includes a length of tubing 32 having a proximal end 34 and an open distal end 36, with the distal end opening being four uniformly laterally disposed apertures as exemplified by aperture 40. Immediately behind the distal end 36 is an inflatable balloon 38 surrounding a portion of the tubing 32. A first lumen 41 defined by the tubing 32 extends from the proximal end 34 to the distal end 36 for conveying fluid therethrough. A second lumen 42 is disposed within the tubing 32 and is accessible via an open proximal end 44 situated in connector tubing 47. The second lumen 42 has an open distal end 46 leading to the interior 48 of the balloon 38 for passage of fluid to inflate or deflate the balloon 38.

A third lumen 45 is disposed within the tubing 32 and is accessible via an open proximal end 50 situated distally from the proximal end of the tubing 32 in lateral connector tubing 43. The third lumen 45 has an open distal end 52 at the distal tip 54 of the tubing 32, and creates a working channel that can accommodate an endoscope 56 or a similarly sized surgical instrument. In certain embodiments, the distal end 58 of the endoscope 56 projects beyond the distal tip 54 a distance sufficient to provide beneficial viewing, tissue engagement, and/or proximity to create a desired diagnostic or therapeutic result. In some embodiments, the first lumen 41 and third lumen 45 do not remain separate throughout their length but rather merge into a common central lumen distally past hub 25. As such, the elongate tubular body distal to the proximal ports, in some embodiments, has exactly 2 lumens, or no more than 2 lumens (a balloon inflation lumen and a fluid/urine/instrument lumen). A configuration allowing for a reduced number of lumens can means less boundary walls may be necessary, advantageously reducing the outside diameter of the catheter that is being passed through the patients' urethra. One benefit of the smaller outside diameter is that it can reduce pain and discomfort for the patient relating to the catheter.

Operation of the catheter 30 is commenced by first positioning the distal end 36 at a desired site usually within a cavity such as a urinary bladder. When desired placement is attained, fluid such as a saline solution is introduced into the second lumen 42 for travel to the interior 48 of the balloon 38 and inflation thereof and retention of the catheter 30 in place. Once so situated, the catheter 30 permits free fluid flow from and/or to the site of its distal end 36. To visually inspect the site of the distal end 36 of the catheter 30, an endoscope 56 is inserted into the third lumen 45 and advanced until its distal end 58 resides beyond the distal tip 54 of the tubing 32. Such advancement results in engagement of the port connector 60 and endoscope connector 62 for releasable retention of the endoscope 56 for use in viewing the catheterized site. In this manner, a physician or other healthcare worker can endoscopically view a site without first removing a catheterized site. In this manner, a physician or other healthcare worker can endoscopically view a site without first removing a catheter treating that site.

4-Way Catheters

Figure 5:
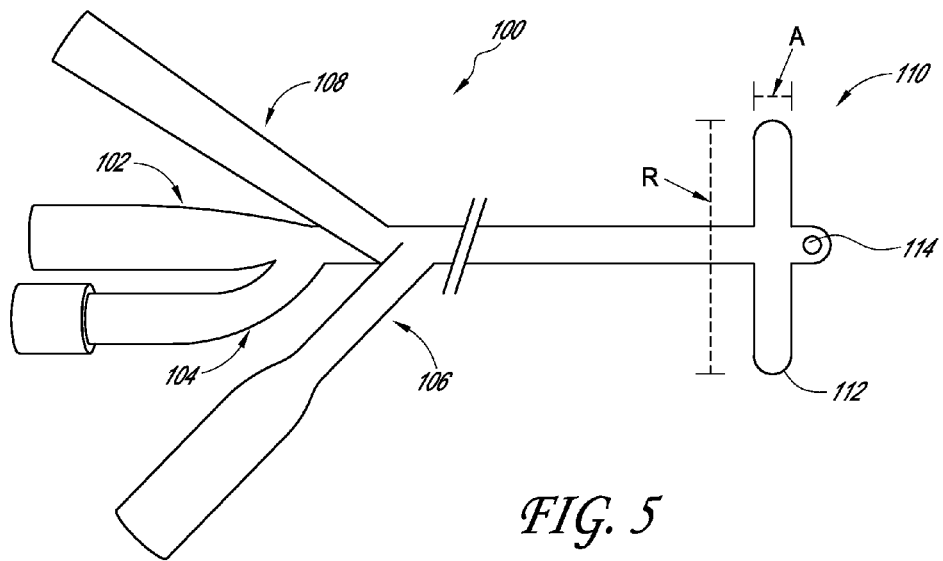
FIG. 5 illustrates a four-way cystoscopy catheter, according to some embodiments.

In some embodiments, disclosed herein is a 4-way cystoscopy catheter 100 designed to better allow cystoscopic evaluation of the bladder through an indwelling transurethral catheter, one embodiment of which is disclosed schematically in FIG. 5. In some embodiments, the device is a modification of the traditional 3-way urethral catheter, having four or more ports. However, low profile balloons as described herein can also be used in conjunction with conventional Foley and 3-way Foley catheters. The catheter body can be made of Silastic, latex, silicone, Teflon, or any other appropriate material. A first port can be a central port 102 having a one-way valve (not shown) that can be built in and designed to accommodate one or more diagnostic and/or therapeutic instruments, such as an endoscope, e.g., a cystoscope, such as a diagnostic cystoscope. The port 102 can advantageously serve as a protective channel to reduce the risk of friction and other trauma caused by placing an instrument directly into the urethra. In some embodiments, the instrument could be a catheter configured to emit energy, such as RF, microwave, laser, X-rays, ultrasound, thermal, and/or other types of energy. In some embodiments, the instrument could be a stiffening member, such as a wire, for use in, for example, an incontinence or prolapse treatment procedure in order to manipulate the anatomical location of the urethra while placing a mesh or another implant in another anatomical structure. In some embodiments, a first instrument is placed within the central lumen of the catheter and then removed, and then a second instrument is placed within the central lumen of the catheter.

A second port can be a balloon inflation port 104; a third port can be a drainage port for urine 106; and a fourth port 108 can be a fluid inflow port. In some embodiments, ports 102, 106, 108 can be fluidly connected to a single lumen, e.g., a central lumen in communication with one, two, or more apertures 114 on the distal end of the catheter, such that the catheter 100 has exactly 2 lumens (the central lumen and the balloon inflation lumen) distal to the proximal ports. In some embodiments, one or more ports 102, 106, 108 can each have discrete lumens each ending distally in separate apertures 114 or a common aperture. In some embodiments, the central lumen could have a size of about or no more than about 22 French, 21 French, 20 French, 19 French, 18 French, 17 French, 16 French, 15 French, or 14 French. The apertures 114 can be spaced along a sidewall of the distal end 110 of the catheter 100 and/or be distal-facing coaxial with the longitudinal axis of the catheter 100, and be the same or different sizes. In some embodiments, the catheter 100 has a single, e.g., no more than one aperture (e.g., exit port). In some embodiments, the single aperture is distally-facing and has the same or substantially the same diameter as that of the central lumen, which can advantageously eliminate the need for additional drainage apertures at the distal tip, potentially reducing catheter length required as well as manufacturing costs.

In some embodiments, the central lumen can have a constant or substantially constant diameter throughout its entire length. The larger diameter single exit port can in some cases reduce the risk of obstruction from the particulates often seen within the bladder. In some embodiments, the exit port can include a mesh, filter, or other mechanism to further reduce the risk of obstruction from particulate matter. In some embodiments, the central lumen, outer diameter, and/or other portions of the catheter can include a therapeutic agent, such as an anesthetic agent, an anti-coagulant (e.g. heparin), an anti-inflammatory, an antimicrobial, and the like. Balloon inflation port 104 can be fluidly connected to a discrete balloon inflation lumen terminating at or near the distal end 110 of the catheter 100 within an expandable member such as a balloon 112, which can be a conventional spherical balloon or a low profile balloon in some embodiments. The balloon shape could be, for example, round, oval, flat, or cylindrical; symmetric or asymmetric along an axial, radial, or other axis. The low profile balloon 112 can be reversibly movable from an unexpanded to an expanded configuration by injection or removal of fluid from the balloon inflation port 104. Low profile balloon 112 can have an expanded radial dimension R that is at least about, about, or no more than about 1.25×, 1.5×, 1.75×, 2×, 2.5×, 3×, 4×, 5×, 6×, 7×, 8×, 9×, 10×, 12×, 15×, 20×, or more of the expanded axial dimension A (and/or height dimension) of the balloon 112, and sometimes have a "pancake"-like shape. In some embodiments, the expanded axial dimension A of the balloon 112 is about 10-20 mm, such as about or less than about 20 mm, 15 mm, or 10 mm. In some embodiments, the expanded axial dimension A of the balloon 112 is larger, such as about 25 mm, or about or less than about 30 mm, 28 mm, 26 mm, 24 mm, or 22 mm.

In some embodiments, a balloon is a flat pancake-shape (i.e., the depth is less than the width; e.g., by a ratio of at least about, about, or no more than about 2:1, 3:1, 4:1, 5:1, 6:1, 7:1, 8:1, 9:1, 10:1, 20:1, or more). In some embodiments, a pancake-shaped balloon is wider than it is deep (e.g., at least about, about, or no more than about 1.5× wider than deep; 2× wider than deep; 5× wider than deep; 10× wider than deep; 25× wider than deep). In some embodiments, a balloon is tall and narrow (e.g., at least about, about, or no more than about 1.5× taller than wide; 2× taller than wide; 3× taller than wide; 5× taller than wide; 10× taller than wide; 25× taller than wide). The balloon can, in some embodiments, have an inflated volume of about or less than about 30 cc, 10 cc, 5 cc, or 3 cc. A catheter 100 having a low profile balloon can in some cases advantageously provide an improved and more comfortable seal proximate an anatomical site, e.g., the internal urethral orifice and thus prevent leakage around the catheter. In some cases, such a catheter can also advantageously be less view-obstructing/in the way of the cystoscope and as such provide improved visualization during a cystoscopy procedure, for both male and female anatomy.

Figure 6:
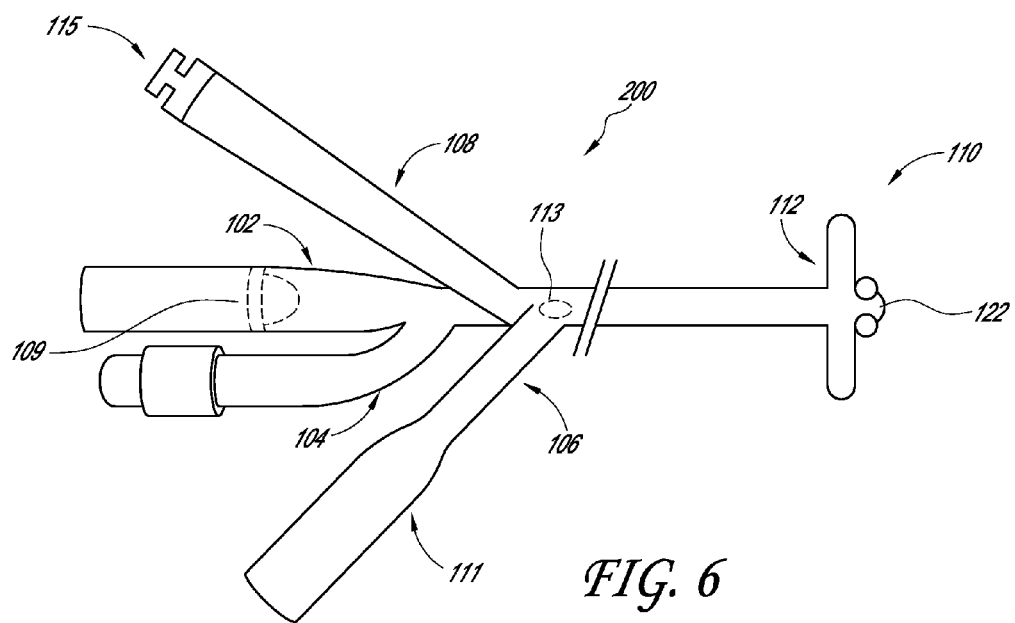
FIG. 6 illustrates another embodiment of a four-way cystoscopy catheter.

FIG. 6 illustrates a 4-way cystoscopy catheter 200 similar to that of FIG. 5, also illustrating a luer or other fitting 115 on the proximal end of the inflow port 108 for connection to an IV bag or another source of media. The instrument, e.g., cystoscope port 102 can include a valve 109 such as a one-way valve present, or other reversible sealing mechanism to prevent the leakage of fluids when the port is not occupied by the cystoscope. The outflow port 106 can include a clamp 111 such as a roller clamp to reversibly allow for urine/media drainage from the body lumen such as the bladder. As with the embodiment in FIG. 5, ports 102, 106, 108 can be fluidly connected to a single lumen in communication with a central lumen 113. The distal end 110 of the catheter can again have a balloon 112 such as a low-profile balloon, but the distal tip 122 could have rounded corners 117 to decrease the potential for trauma, or another configuration as shown close-up and described in connection with FIGS. 7A-7E below.

FIGS. 7A-E illustrate various embodiments of distal tip 122 catheter configurations with blunt tips to reduce or avoid trauma associated with the distal tip and/or cystoscope. Also illustrated is balloon 112 in an uninflated state on or near the sidewall of the distal end catheter, and an aperture 114 that can be distally facing and/or on a sidewall as previously described. As illustrated in FIG. 7A, include a distal tip 117 embodiment having rounded edges. FIG. 7B illustrates a distal tip embodiment 119 having a beveled edge. FIG. 7C illustrates a distal tip configuration having an end cap 123 surrounding the distally facing surface of the distal tip. The end cap 123 can include one or more slit patterns 121, such as a star pattern 121"", linear pattern 121', cross pattern 121", V or W pattern (not shown), Y pattern 121''', or others. The end cap 123 with slits 121 can advantageously provide a safety feature and also protect an endoscope while retracted within the catheter. Also shown are one, two, or more apertures 114 for media infusion and or drainage along the sidewall. FIG. 7D illustrates an embodiment of a contoured distal tip 125 having an internal bevel (with a decreasing axial length from a lateral to medial direction). FIG. 7E illustrates an embodiment of a contoured distal tip 127 having an external bevel (with an increasing axial length from a medial to lateral direction).

Figure 8:
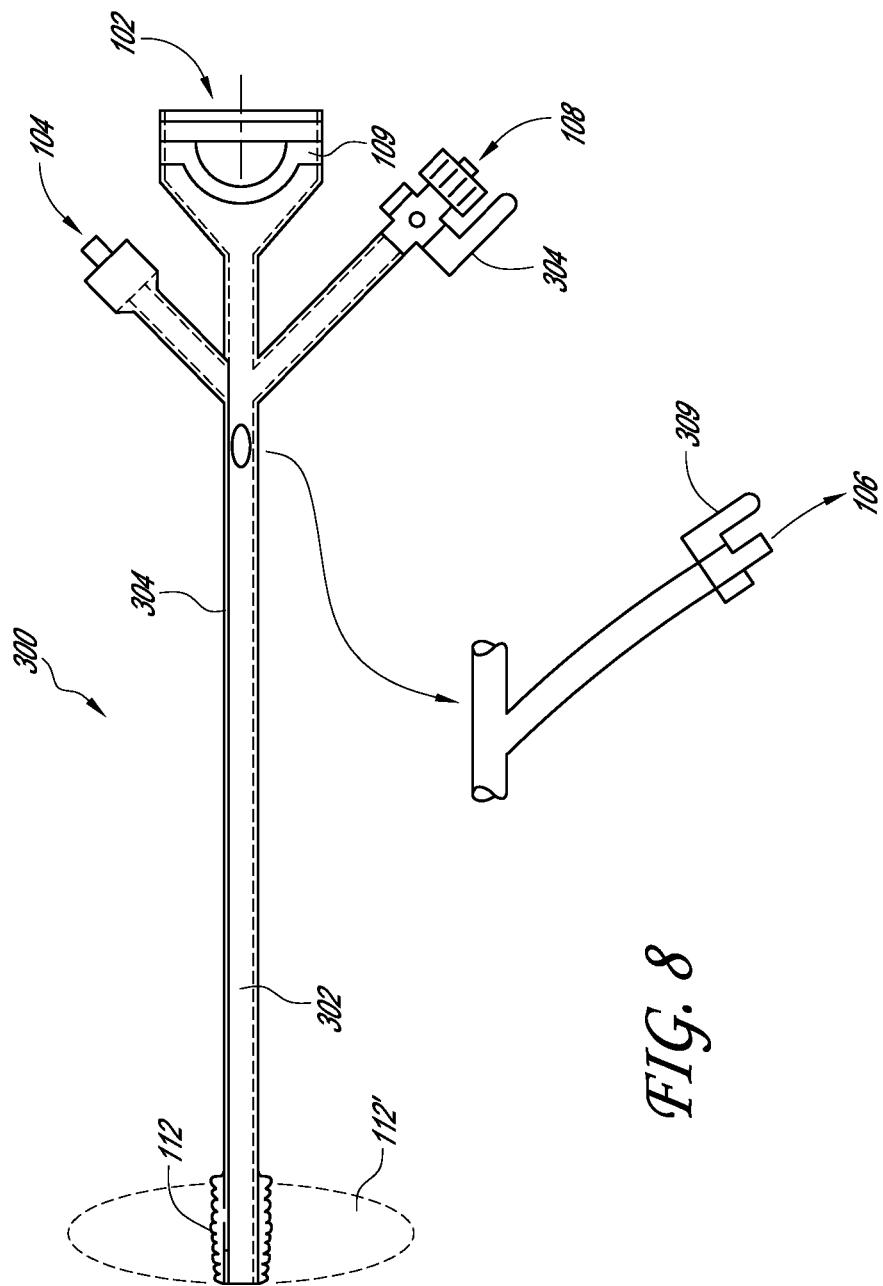
FIG. 8 illustrates another embodiment of a 4-way cystoscopy catheter.

FIG. 8 illustrates another embodiment of a 4-way cystoscopy catheter 300, illustrating an endoscope port 102 at the proximal-most end and coaxial with the longitudinal axis of the catheter 300. Endoscope port 102 can include a valve 109 or other seal in the port lumen as previously described. Also illustrated are inflow ports 108 and outflow ports 106 which can include a luer lock and/or stopcock-type valve 309 as shown to regulate fluid inflow and outflow, respectively. In some embodiments, the ports can have indicia for enhanced identification, such as be differing colors. Ports 102, 106, 108 can also all be in fluid communication with a central lumen 302 as previously described. Also shown is balloon inflation port 104 which can be in communication with a discrete balloon inflation lumen 304 separate from the central lumen 302. Balloon inflation lumen 304 can be in turn be connected to a balloon 112 which can be a conventional or low profile, e.g., "pancake" type balloon as previously described, and shown in an uninflated 112 and inflated configuration 112' (in phantom).

Scope Port Features

FIGS. 9A-9D illustrates an embodiment of a keyed catheter scope port 401 and its attachment to an endoscope 420, such as a cystoscope. FIG. 9A is a side view of scope port 401 including one, two, or more alignment pins 402 and internal seal or valve 404 across the scope port lumen 406. The alignment pin 402 could include indicia, such as a color to match with corresponding indicia on an endoscope pin slot 402. FIG. 9B illustrates an end view of the scope port 102 illustrated in FIG. 9A. FIG. 9C is a side view of the endoscope 420 showing scope proximal portion 422 which can be operably connected to a light post 408. Also illustrated is scope hub 406 including one, two, or more pin slots 404 complementary to and configured to reversibly mate with the alignment pins 420. Other locking mechanisms other than pins and slots are also within the scope of the disclosure. FIG. 9D is a top view of the embodiment of FIG. 9C. The keyed catheter system can be advantageous in some embodiments to help provide spatial orientation of certain anatomical landmarks while navigating the endoscope within the body. For example, using the orientation of a pin-slot combination as a guide relative to a clock face, an operator could identify the left ureter with respect to a right ureter. Furthermore, such embodiments can still advantageously allow for relative movement between the scope and the catheter.

Figure 10A:
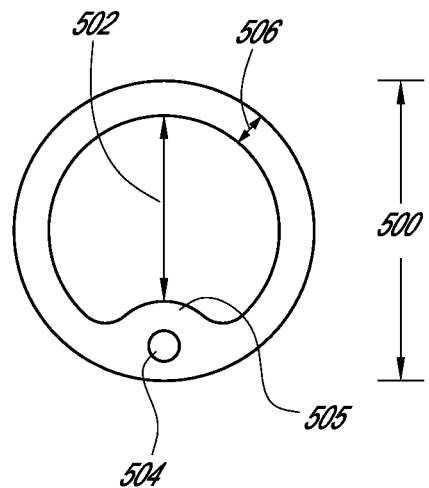
FIGS. 10A-10B illustrate cross-sections through a balloon catheter, according to some embodiments.
Figure 10B:
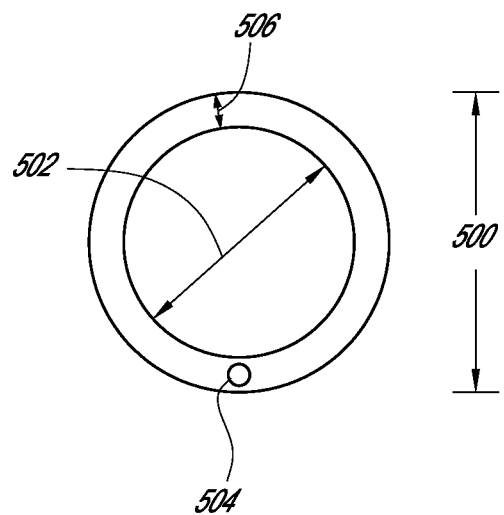

In some embodiments, a catheter could have an elongate shaft portion of which the outer diameter 500 of the shaft is between about 5 mm and about 7 mm, such as about 6 mm. The inner diameter 502 of the central lumen could be, for example, about 2 mm about 4 mm, such as between about 2.3 mm and about 2.6 mm, or between about 3.0 mm and about 3.5 mm. The central lumen could, for example, have a circular cross-sectional area as illustrated in FIG. 10B, or could have a localized raised area 505 to provide more room for the balloon inflation lumen 504 as illustrated in FIG. 10A. The balloon inflation lumen 504 could, for example, have a diameter of between about 0.6 mm and about 1.2 mm, or between about 0.8 mm and about 1.0 mm for example. The shaft sidewall could have a thickness 506 of between about 1 mm and about 2 mm, such as between about 1.2 mm and about 1.5 mm, for example.

Steerable Catheter

FIGS. 11A-11D illustrates an indwelling catheter that can be steerable and curvable via a deflectable distal end. Catheters as described herein could be configured to house a rigid rod lens scope (e.g., a 70 degree scope) or a flexible fiber scope (e.g., a 0 degree scope). FIG. 11A illustrates a steerable catheter 900 having any of balloon inflation port 104, inflow port 108, outflow port 106, and scope ports 102 with valve/seal 109 that can be as previously described. At the proximal end or along the shaft of the catheter can be a deflection control 700 for deflecting the distal end of the catheter through a controllable angular range. The deflection control 700 could be, for example, a rotatable knob operably connected to one, two, or more control wires, which travel within control wire lumens 708 and are operably attached at their distal end to the distal end of the catheter, such as at a distal cap 704.

Figure 12:
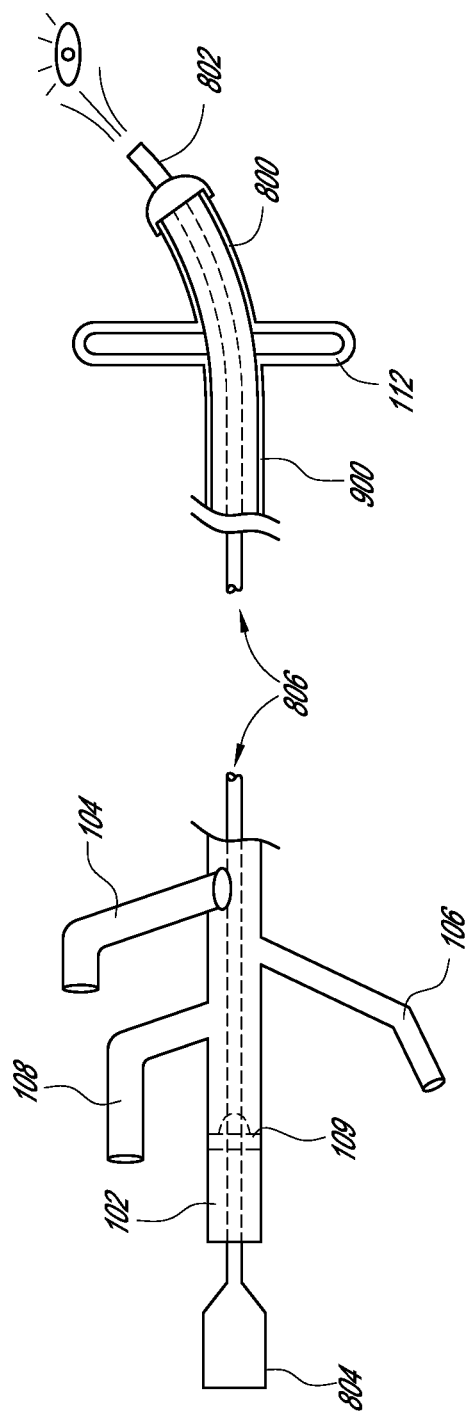

FIG. 11B is a cross-section through line A-A of FIG. 11A, illustrating central lumen 714 with scope 716 therethrough, balloon inflation lumen 712, and control wire lumens 708. FIG. 11C illustrates schematically deflection control 800 having a rotatable knob 703, base 707, and body 705 of which the proximal ends of control wires 702 can be wrapped around. Rotation of the knob 703 in an appropriate direction can move the distal end of the catheter from an undeflected configuration in which the distal end is coaxial with the longitudinal axis of the catheter to a deflected configuration in which the distal end is not coaxial with the longitudinal axis of the catheter. The distal end of the catheter can be configured to deflect up to about 45, 60, 90 degrees, or more. FIG. 11D illustrates a section through the distal end of the catheter, showing catheter sidewall 709 which can be collapsed distally near 713 onto the pullwires 708 as shown, e.g., using heat, and terminating in ball 711. Alternatively, the lumen can be filled with a material such as a resin to lock the wires 708 to the catheter wall 709. FIG. 12 shows the catheter 900 of FIGS. 11A-11D in a deflected configuration, showing a flexible fiber 0 degree scope 804, scope shaft 806, deflected catheter distal tip 800, and scope tip 802 extending beyond the deflected catheter tip 800.

Figure 13:
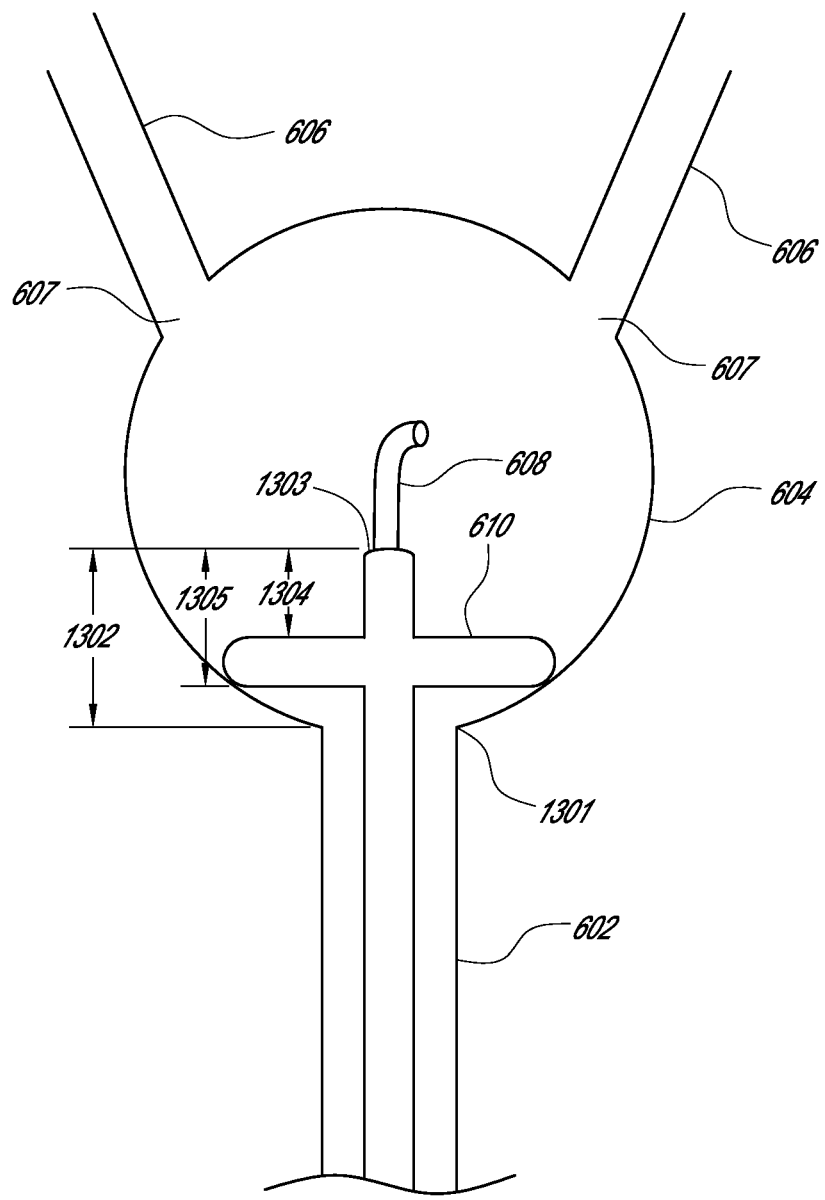
FIG. 13 illustrates schematically an indwelling catheter passing through the urethra and into the bladder with a pancake-shaped balloon in an expanded configuration, and a cystoscope extending distally out of the distal end of the catheter.

FIG. 13 illustrates schematically an indwelling catheter passing through the urethra 602 and into the bladder 604 with a pancake-shaped balloon 610 in an expanded configuration, and instrument such as a cystoscope 608 extending distally out of the distal end 1303 of the catheter. The distal end of the cystoscope can be rigid and coaxial with the longitudinal axis of the catheter, or deflected as shown. Also shown are ureters 606. In some embodiments, a lower profile or pancake-shaped balloon 610 can be desirable to, among other things, reduce or minimize a distance 1302 from the opening into the bladder 1301 to the distal end 1303 of the catheter. It can be desirable in some embodiments to minimize the distance 1302 to enable a larger viewing angle within the bladder 604 and/or to enable viewing of openings into the ureters 607 that may be located closer to the opening into the bladder 1301 than is shown in this schematic view. Further, for similar reasons (e.g., maximizing or increased viewing angle range), it can be advantageous in some embodiments to minimize or limit a distance 1304 from the distal end 1303 of the catheter to a distal end of the balloon 610 and/or a distance 1305 from the distal end 1303 of the catheter to a proximal end of the balloon 610. In some embodiments, the distal end 1303 of the catheter is flush with the distal end of the balloon 610. In other embodiments, the distal end 1303 extends beyond the distal side of the balloon 610 by no more than about 0.5 mm, 1.0 mm, 1.5 mm, 2.0 mm, 2.5 mm, 3.0 mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm, 10.0 mm, 10.5 mm, 11.0 mm, 11.5 mm, 12.0 mm, 12.5 mm, 13.0 mm, 13.5 mm, 14.0 mm, 14.5 mm, 15.0 mm, 15.5 mm, 16.0 mm, 16.5 mm, 17.0 mm, 17.5 mm, 18.0 mm, 18.5 mm, 19.0 mm, 19.5 mm, or 20.0 mm. This measurement 1304 is taken with reference to the distal-most point of the balloon. In some embodiments, this measurement is the same whether the balloon is in an expanded or an unexpanded configuration. In some embodiments, however, the balloon is configured to expand in both a transverse and an axial direction when changing from an unexpanded to an expanded configuration. In that case, the measurement 1304 from the distal-most point of the balloon to the distal end of the catheter may be smaller when the balloon is in an expanded configuration than when the balloon is in an unexpanded configuration. In some embodiments, the measurement 1305 from the distal end 1303 of the catheter to the proximal side of the balloon is about or no more than about 10.0 mm, 10.5 mm, 11.0 mm, 11.5 mm, 12.0 mm, 12.5 mm, 13.0 mm, 13.5 mm, 14.0 mm, 14.5 mm, 15.0 mm, 15.5 mm, 16.0 mm, 16.5 mm, 17.0 mm, 17.5 mm, 18.0 mm, 18.5 mm, 19.0 mm, 19.5 mm, 20.0 mm, 20.5 mm, 21.0 mm, 21.5 mm, 22.0 mm, 22.5 mm, 23.0 mm, 23.5 mm, 24.0 mm, 24.5 mm, 25.0 mm, 25.5 mm, 26.0 mm, 26.5 mm, 27.0 mm, 27.5 mm, 28.0 mm, 28.5 mm, 29.0 mm, 29.5 mm, or 30.0 mm.

Port-Selecting

In some embodiments, a urinary access catheter comprise a valve or other control element, for example, a 3-way valve, that provides the ability to select a specific port, for example, any one of three ports, to utilize during a procedure. For example, a physician can select between inflow, outflow, and scope insertion ports as necessary to complete the procedure.

Figure 14A:
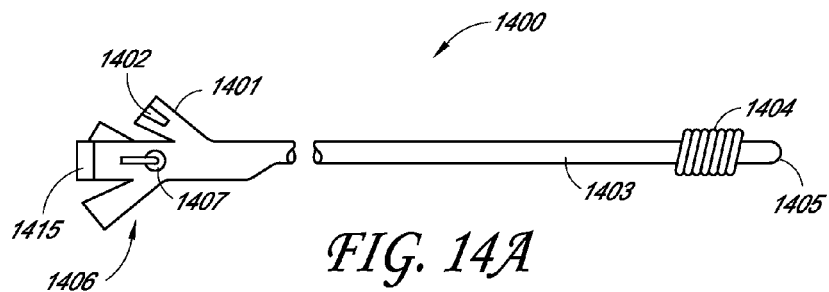
FIGS. 14A and 14B illustrate an embodiment of a catheter comprising a port selection valve.
Figure 14B:
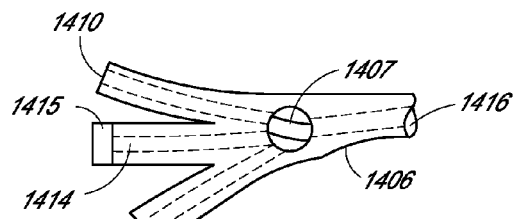

FIGS. 14A and 14B illustrate an example embodiment of a catheter 1400 comprising a 3-way valve 1407 that enables selective connection of an inflow lumen 1410, an outflow lumen 1412, or a scope lumen 1414 to a single main lumen 1416. FIG. 14A is a top view of the catheter 1400, which comprises a port assembly 1406 at a proximal end, connected through an elongate shaft 1403 to a distal tip 1405 and a balloon 1404 positioned near the distal tip 1405. FIG. 14B is a detail view of the port assembly 1406. In some embodiments, the catheter 1400 also comprises one or more seals or other valves, such as valve 1402 connected to the balloon inflation port 1401, and seal 1415 at or near the proximal opening of the scope lumen 1414. In some embodiments, the proximal port assembly 1406 comprises at least two ports, one of which is sealed for the insertion of a viewing instrument, and a second for the transport of fluids into or out of the bladder. In some embodiments, the fluid ports are separated into independent connections for inflow and outflow to enable separate control of each.

Figure 15:
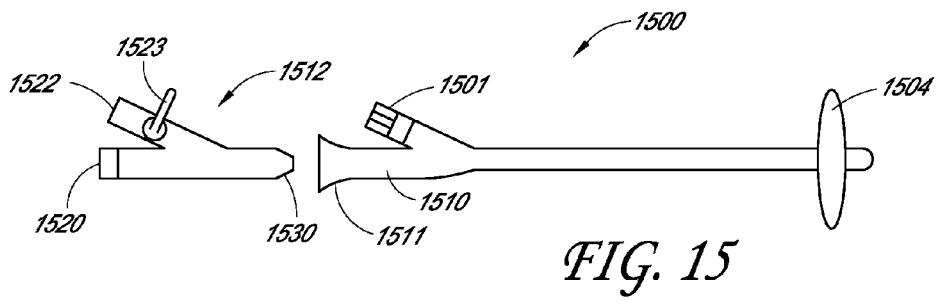
FIG. 15 illustrates an embodiment of a catheter comprising a detachable port assembly.

In some embodiments, a urinary access catheter includes only two ports: one for the inflation/deflation of the distal balloon and a second port that serves multiple functions—a standard drainage funnel and as a connecting port for an accessory port expansion adapter. FIG. 15 illustrates such an embodiment, wherein catheter 1500 comprises a port housing 1510 configured to be coupled with a detachable port assembly 1512. The catheter 1500 further comprises a balloon 1504 (shown inflated), a balloon inflation portion 1501, and a funnel 1511 shaped to guide insertion of the coupling end 1530 of the port assembly 1512 into the port housing 1510. The port assembly 1512 comprises a scope port 1520, an inflow/outflow port 1522, and a flow control valve 1523 configured to selectively fluidly couple the port 1522 to the catheter 1500. One advantage of the embodiment illustrated in FIG. 15 is that the post-procedure assembly that the patient will observe has been reduced or minimized, improving patient comfort and compliance.

In other embodiments, the port housing 1510 may not comprise a funnel 1511 and/or may comprise a different shape and/or connecting means to aid in coupling the port assembly 1512 to the catheter 1500.

Electronic Visualization

Figure 16:
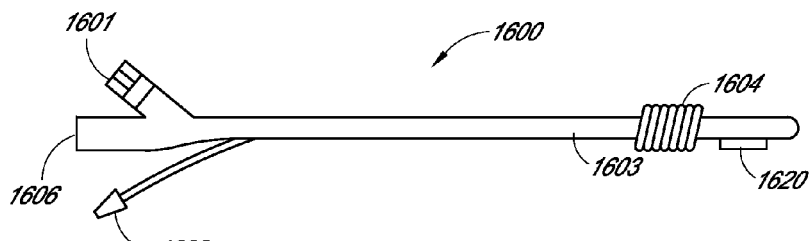
FIG. 16 illustrates an embodiment of a catheter comprising an electronic sensor.

In some embodiments, a sensor or other electronic visualization assembly, for example, a CCD chip, is attached to the distal end of the catheter to add visualization to the catheter itself. This can be advantageous to, among other things, enable visualization without requiring the insertion of a cystocope. FIG. 16 illustrates such an embodiment, whereby the visualization is provided by a sensor 1620, such as an integral CCD chip, CMOS chip or equivalent. As such, a separate scope port need not be present (although in some embodiments, both electronic visualization and a scope port may be provided). The catheter 1600 illustrated in FIG. 16 further comprises a shaft 1603, balloon 1604 fluidly connected through the shaft 1603 to a balloon inflation port 1601, a fluid port 1606, and a camera connector 1602. The camera connector 1602 may comprise, for example, a USB or other type of electrical connector that enables transmission of information from the sensor 1620. In this embodiment, the overall envelope or outer diameter of the device shaft 1603 can be reduced, because the shaft 1603 does not need to be configured to allow insertion of a cystoscope, improving patient comfort and ease of passage.

Scope Retention and/or Orientation Features

In some embodiments, a urinary access catheter includes a retention and/or orientation feature, for example, a band, that can be separately attached to the catheter or, in some embodiments, integrally molded, that will bind the endoscope to the catheter to enable the endoscope and the catheter to substantially translate and rotate together as a single element. In such an embodiment, a physician can insert the scope and connect or couple the band to a structure of the scope, for example, a light post of the scope. By virtue of the location of the band and the light post, it will insure that the scope and catheter are properly orientated with respect to each other and that they have been indexed to the proximal surface of the mating scope introduction port. In some embodiments, a retention feature, such as a band, is used for retaining the scope, but is not necessarily used to align the scope rotationally with respect to the catheter.

Figure 17:
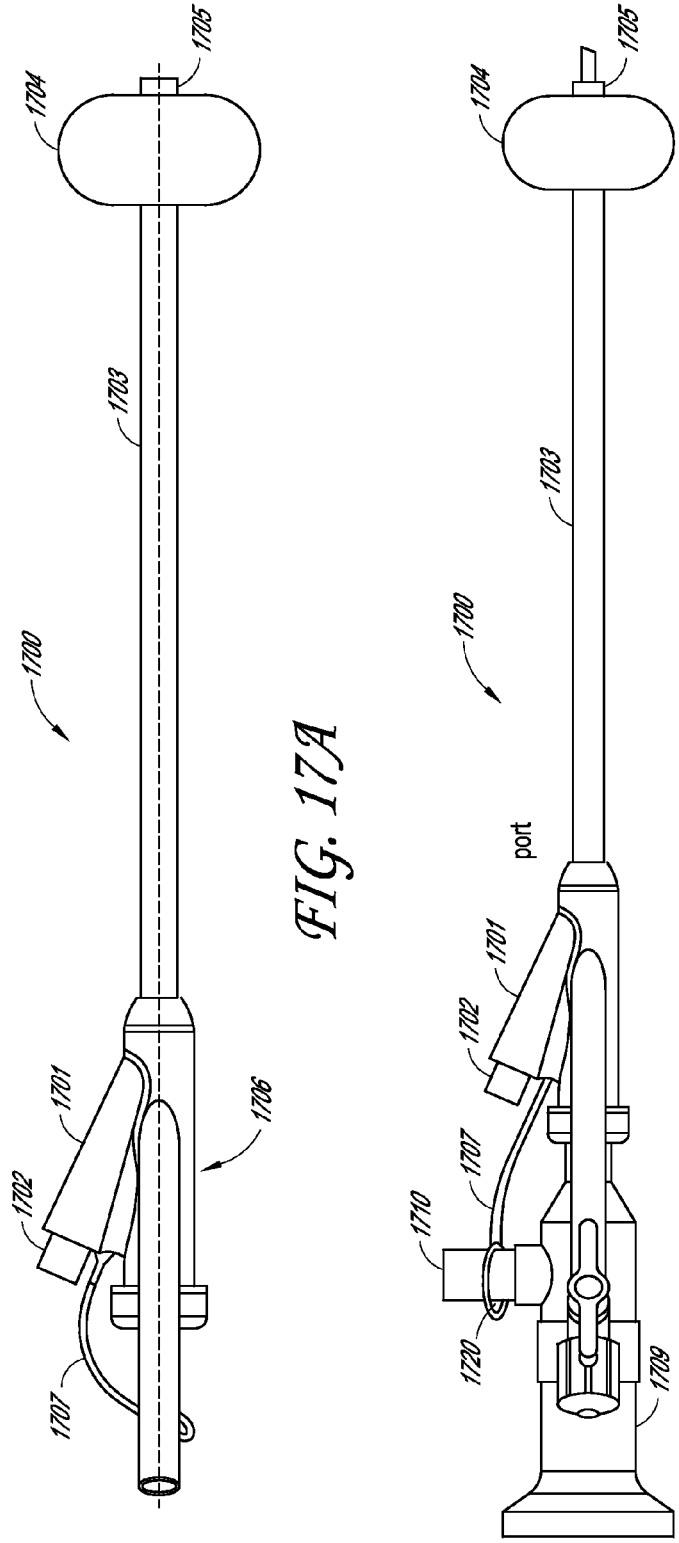
FIGS. 17A and 17B illustrate an embodiment of a urinary access catheter comprising a scope retention and/or orientation member.

FIGS. 17A and 17B illustrate an embodiment of a urinary access catheter 1700 with a distal balloon 1704 for stabilization of the catheter within the bladder, a catheter shaft 1703, and a proximal entry housing 1706, which comprises a one way valve 1702 for the inflation of the balloon. A shaft 1703 of sufficient length is present so that the housing 1706 is located outside the body when the distal end is in position in the bladder. The proximal port assembly 1706 comprises a plurality, such as 2, 3, 4, or more ports, one of which is sealed for the insertion of a viewing instrument, and at least a second port for the transport of fluids into or out of the bladder. In some embodiments, the fluid ports are separated into independent connections for inflow and outflow to enable separate control of each. A flexible, integrally molded band 1707 can be utilized to attach the scope to the catheter.

The catheter 1700 comprises a balloon inflation port 1701, in which is located the valve 1702, and a soft, flexible distal tip 1705. In this embodiment, the port assembly 1706 includes an integrally molded band 1707 that allows the user to selectively bind the catheter 1700 and the scope 1709 using scope light post 1710 or another attachment structure. One end of the band 1707 may be connected to the catheter (either permanently or non-permanently), with another end of the band 1707 comprising an aperture 1720 configured to attach to the light post 1710. In some embodiments, the band 1707 can have, instead of or in addition to the aperture 1720, for example, complementary reversible locking mechanisms, clips, hook-and-loop fastener, or other types of attachment features. The end of the band 1707 connected to the catheter 1700 can be attached, for example, to part of the inflation port 1701, port assembly 1706, shaft 1703, or another structure of the catheter.

Sealing and Fluid Flow Control Features

In some embodiments, a urinary access catheter comprises one or more caps, such as, for example, integrally molded sealing caps, to close off the inflow and/or drainage (outflow) ports of the catheter. In some embodiments, the flow of fluids into and/or out of the patient can be controlled by the sealing caps, eliminating any need for separate control members. In some embodiments, a drainage tube can be inserted into the drainage port, disabling the ability of the drainage port sealing cap to seal and/or control flow. Thus, in some embodiments, a second control member, for example a slide clamp, can be added to enable independent or additional control of the fluids. In some embodiments, the drainage port and catheter hub can be fully constructed with one end captivated into the device hub and the proximal end having an expanded funnel to mate with the associated uro drainage bag. Thus, a control device that can be attached post production can be both cost and time efficient.

Figure 18:
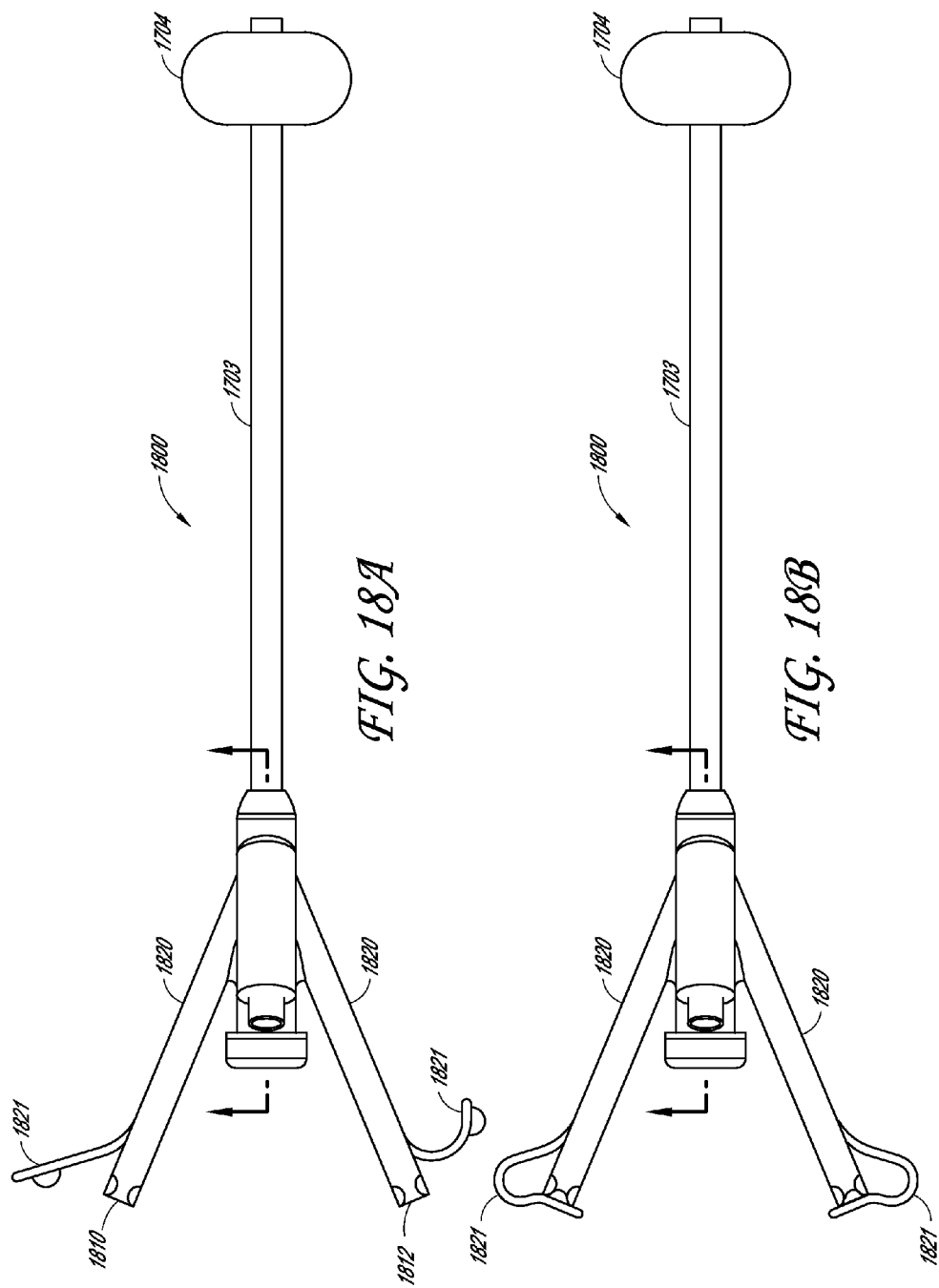
FIGS. 18A and 18B illustrate an embodiment of a urinary access catheter comprising sealing caps.

FIGS. 18A and 18B illustrate an embodiment of a catheter 1800 comprising integral sealing caps 1821 for the inflow and outflow (drainage) ports, 1810 and 1812. In FIG. 18A, the sealing caps 1821 are shown in an open (e.g., non-sealed) configuration. In FIG. 18B, the sealing caps 1821 are shown in a closed (e.g., sealed) configuration. In some embodiments, the sealing caps 1821 are configured to couple to the inflow and outflow ports 1810, 1812 using friction. In some embodiments, the caps are configured to couple using a threaded junction or other attaching and/or sealing mechanism. One benefit of an embodiment such as is shown in FIGS. 18A and 18B is that the mass of the post-procedure device that the patient may observe in the recovery room may be reduced or minimized, improving patient comfort and compliance. Another benefit is reduced overall cost of the device, such as by having the sealing caps integrally molded, instead of needing separate components.

Figure 19:
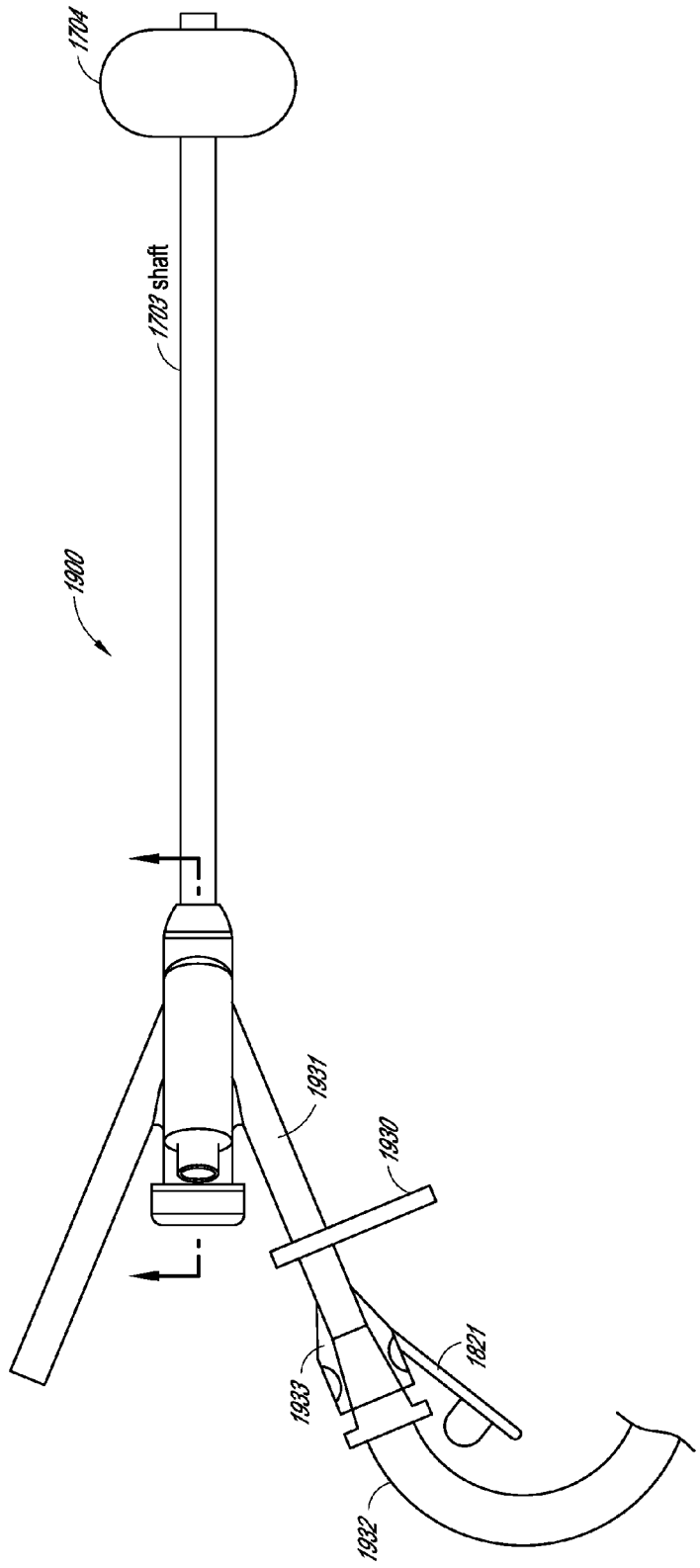
FIG. 19 illustrates an embodiment of a urinary access catheter comprising primary and secondary sealing features.

FIG. 19 illustrates an embodiment of a catheter 1900 comprising a secondary fluid control device 1930, for example a slide clamp. The slide clamp 1930 is coupled to the drainage port tubing 1931. This configuration may be advantageous to enable, for example, a physician to control fluid drainage when a uro drainage bag tube 1932 has been inserted into the drainage port 1933, disabling the sealing cap 1821.

Although the secondary fluid control device 1930 of the catheter 1900 is a slide clamp, various secondary fluid control devices may be used. FIGS. 20A through 20E illustrate various examples of fluid control devices that may be utilized. FIGS. 20A and 20B illustrate open jaw slide clamps 2010 and 2020 that can be placed on the tubing and can be adjusted to pinch the tubing closed by sliding the tubing into the narrowing slot 2012, 2022. FIG. 20C illustrates a pinch clamp or closure clamp 2030 that can attach to the tubing by open slots on each end and can seal the tubing by the intersection of two opposing plates or clamping surfaces 2032, 2034. FIG. 20E illustrates a similar pinch clamp or closure clamp 2080 comprising opposing clamping surfaces 2082, 2084. The clamp 2080 also comprises a slot 2086. The slot 2086 may be used, for example, to at least temporarily attach the clamp 2080 to a catheter as disclosed herein. For example, cohesion tape or another suitable tape or other fastener may be utilized to at least temporarily retain the clamp 2080 to a shaft or other feature of a catheter during packaging, shipping, and/or the like. In some embodiments, a catheter as disclosed herein, along with a clamp 2080 temporarily affixed thereto comprises a kit. In some embodiments, cohesion paper or tape is a beneficial fastener to use to temporarily attach the clamp 2080 to the shaft of the catheter, because the tape is strong enough to keep the clamp 2080 retained to the catheter, but is relatively easy to remove, for example, with just a tug on the tape, and leaves little or no residue on the catheter and/or clamp 2080. Further, some other clamp styles may appear cumbersome when attached to the catheter and/or may contact a patient's skin or be difficult to work with when dealing with obese patients. Further, larger, and/or more intrusive clamps, and/or a clamp more permanently installed on the catheter may impact the packaging of a catheter or catheter kit and pose a risk for package damage due to having, for example, sharp corners or edges. Accordingly, it can be advantageous to have a removable style clamp, such as the clamp 2080, that is not positioned around a port's tubing during packaging and shipping, but is still able to be somehow at least temporarily affixed to the catheter to form a catheter kit. It can be advantageous to have the clamp at least temporarily affixed to the catheter to keep the clamp from being separated from the catheter and/or falling out of the packaging when the packaging is opened in a sterile environment. FIG. 20D illustrates four ramp tubing clamps 2040, 2050, 2060, 2070. A ramp tubing claim can be assembled over the tubing and the translation of the cylindrical roller 2042 along its defined pathway will collapse the tubing, sealing it off to fluid flow.

Multi-Connector Capability and Other Features

Figure 21C:
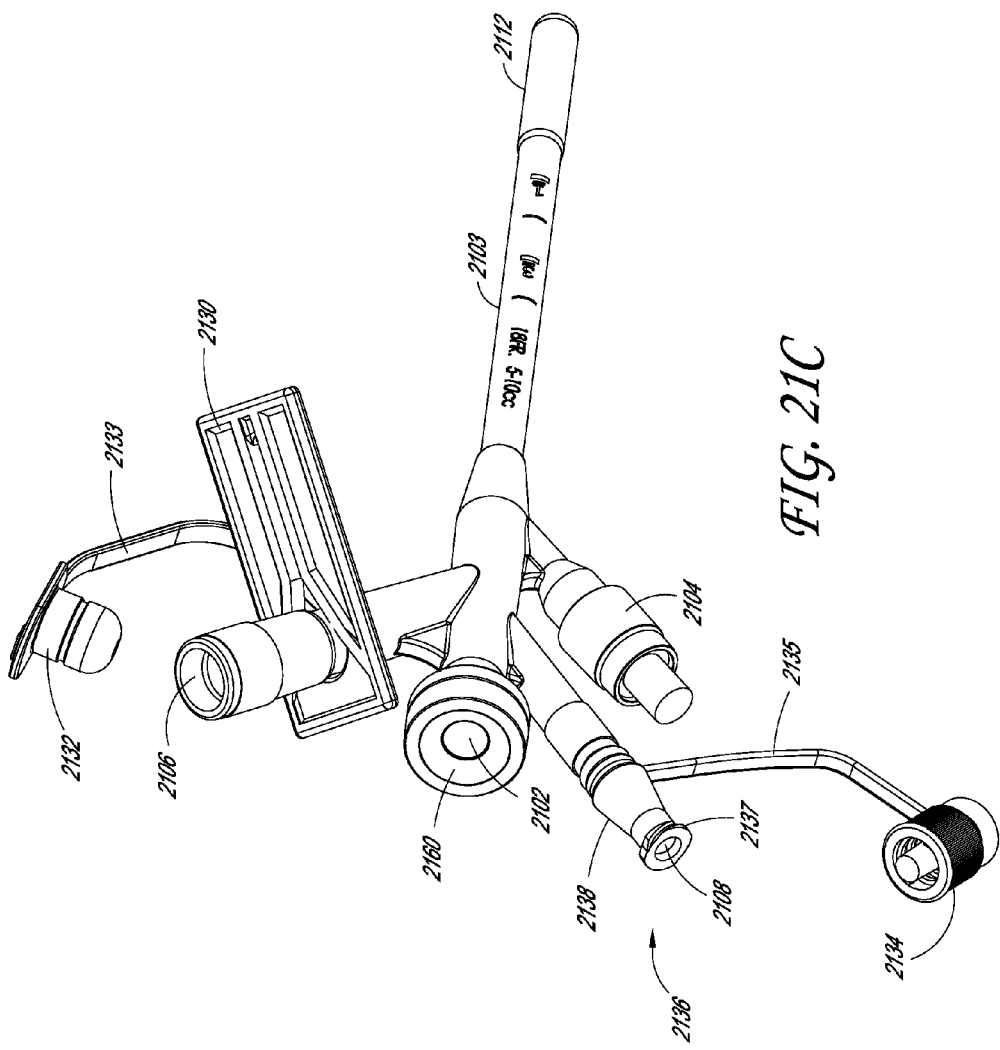

FIGS. 21A through 21D illustrate another embodiment of a urinary access catheter 2100 configured to enable cystoscopy without removing the catheter from the bladder. The embodiment illustrated in FIGS. 21A through 21D is similar to other embodiments disclosed herein, but also has additional advantageous features. FIG. 21A is a top view of the catheter 2100, with the balloon 2112 in an uninflated configuration. FIG. 21B is a top view of the catheter 2100 with the balloon 2112 in an inflated configuration. FIG. 21C is a perspective view of the catheter 2100. FIG. 21D is a cross-sectional view of the shaft 2103 of the catheter 2100, the section taken as shown in FIG. 21A at the junction between an interior cavity of the balloon 2112 and the balloon inflation lumen 2113.

The catheter 2100 comprises a proximal portion 2170 comprising a plurality of ports, the proximal portion 2170 being connected to the balloon 2112 via a shaft 2103. The shaft 2103 in this embodiment comprises a plurality of markings 2107 configured to illustrate a distance away from a proximal end 2117 of the balloon 2112. As discussed above, it can be advantageous in some embodiments to reduce the distance the distal tip 2105 of the catheter 2100 extends within the bladder, to enable a larger viewing angle within the bladder. Accordingly, the markings 2107 can be useful to, among other things, enable a physician to determine how far the distal tip 2105 and/or the balloon 2112 is extending within the bladder and/or the relative position of the catheter 2100 with respect to the bladder.

The proximal portion 2170 of the catheter 2100 comprises a central port 2102, for example, for insertion therethrough of a cystoscope, a balloon inflation port 2104, a drainage port 2106, and a fluid inflow port 2108. In some embodiments, the central port 2102, drainage port 2106, and fluid inflow port 2108 are all in fluid communication with a single central lumen 2105, illustrated in FIG. 21D. The central port 2102 may comprise a seal or one-way valve, as is illustrated in other embodiments disclosed herein, to enable the central port 2102 to remain sealed when a cystoscope or other instrument is not inserted therethrough. The seal may also be utilized to keep the central port 2102 from leaking when a cystoscope and/or another instrument is inserted therethrough. The balloon inflation port 2104 may comprise a one-way valve or other sealing or control mechanism to enable control of fluid inflow to and outflow from the balloon inflation lumen 2113.

The drainage port 2106 in this embodiment comprises two sealing features (e.g., redundant sealing features), similar to as described above with reference to FIG. 19. In this embodiment, the catheter 2100 comprises a cap 2132 attached to the drainage port 2106 using a tether 2133. In some embodiments, the cap 2132 and/or tether 2133 are integrally molded to the catheter 2100, which can be advantageous to, among other things, reduce cost and size of the catheter 2100. The cap 2132, similar to the cap 1821 illustrated in FIG. 19, can be used to seal the drainage port 2106. In some cases, however, another tube or connector (such as from a drainage bag) may be connected to the drainage port 2106, making it not possible or difficult to utilize the cap 2132 to stop or reduce flow through the drainage port 2106. To, among other things, deal with this situation, the drainage port 2106 comprises a second sealing feature, in this case a slide clamp 2130, which enables the drainage port 2106 to be sealed even when the cap 2132 cannot be used.

In the embodiment illustrated in FIG. 21A, the drainage port 2106 further comprises a groove 2131 in which the slide clamp 2130 is positioned. Such a groove 2131 can be advantageous to, for example, retain the slide clamp 2130 to the catheter 2100, even when the slide clamp 2130 is not in a sealed configuration. This can help to limit a possibility that the slide clamp 2130 will fall off of or be removed from the catheter 2100.

The fluid inflow port 2108 of the catheter 2100 comprises a multifunction or dual-use connector 2136 configured to be able to connect with more than one type of mating tubing or connector. In some embodiments, the multifunction connector 2136 is integrally molded to the catheter 2100, which can be advantageous to, among other things, reduce size, complexity, and cost of the catheter. The multifunction connector can, in some embodiments, comprise a plastic, such as, for example, ABS. In some embodiments, the connector 2136 can be attached to the catheter 2100 using an adhesive, friction, insert molding, and/or the like. In this embodiment, the multifunction connector 2136 comprises a threaded region 2137, a tapered region 2138, and an annular region 2139 between the threaded region 2137 and tapered region 2138. The threads 2137 are configured to connect with a mating connector, such as, for example, a Luer connector common to IV tubing. In some embodiments, a connector is configured to seal against the tapered region 2138 by being forced against the tapered region 2138 by the threaded region 2137. However, by including the annular region 2139, which in this embodiment has an outer diameter smaller than an outer diameter of the threaded region 2137, flexible tubing, such as, for example, cysto tubing, that does not include a threaded connector can also seal to the multifunction connector 2136. For example, if the flexible tubing comprises an inner diameter smaller than the outer diameter of the threaded region 2137, the tubing can be passed over the threaded region 2137 and will compress within the annular region 2139. The tubing will seal to the multifunction connector 2136, and resist being removed from the connector, using friction and/or hoop stresses created by being elastically deformed. In some embodiments, the tubing seals at least partially against the tapered region 2138, and the threaded region 2137 helps to keep the tubing from becoming detached from the multifunction connector 2136. In some embodiments, a maximum diameter of the tapered region 2138 is larger than a maximum or outer diameter of the threaded region 2137.

The catheter 2100 further comprises a cap 2134 attached to the catheter 2100 using a tether 2135. In this embodiment, the cap 2134 comprises threads configured to couple with the threads 2137 of the multifunction connector 2136. Accordingly, the threads 2137 can be used with not only a mating drainage connector, but also a cap for sealing the fluid inflow port 2108. In some embodiments, the cap 2134 is configured to mate with and seal upon the tapered region 2138 in addition to or instead of coupling to the threads 2137. It can be advantageous to use a cap to seal the inflow port 2108 to, among other things, mitigate a risk of urine leakage during and/or after surgery.

In some embodiments, an outer diameter 2150 of the central lumen 2105 is approximately 3.2 mm. In other embodiments, the diameter 2150 can be larger or smaller than 3.2 mm, such as, for example, about 2.0 mm, 2.2 mm, 2.4 mm, 2.6 mm, 2.8 mm, 3.0 mm, 3.4 mm, 3.6 mm, 3.8 mm, 4.0 mm, 4.2 mm, 4.4 mm, 4.6 mm, 4.8 mm, or 5.0 mm. In some embodiments, the outer diameter 2152 of the shaft 2103 is about 6.0 mm. In other embodiments, the outer diameter 2152 of the shaft 2103 can be larger or smaller than 6.0 mm, such as, for example, 4.0 mm, 4.2 mm, 4.4 mm, 4.6 mm, 4.8 mm, 5.0 mm, 5.2 mm, 5.4 mm, 5.6 mm, 5.8 mm, 6.2 mm, 6.4 mm, 6.6 mm, 6.8 mm, or 7.0 mm.

In the embodiment illustrated in FIGS. 21A through 21D, all four ports 2102, 2104, 2106, and 2108 are positioned in a single plane. Such a configuration can be advantageous for, among other things, reducing manufacturing costs.

With reference to FIG. 21C, the central port 2102 of the catheter 2100 comprises a tapered region 2160 shaped and configured to enable easier insertion of a cystoscope into the central port 2102. The tapered region 2160 can be tapered such that, if a distal tip of a cystoscope contacts the tapered region 2160, the tapered region 2160 will help to guide the tip of the cystoscope into the central port 2102.

In some embodiments, one or more of the ports of the catheter 2100, or other embodiments disclosed herein, may comprise color-coding to aid in identification of different ports and/or to increase safety. For example, a port may comprise a color-coded band extending around a proximal end of the port. In some embodiments, the inflow/irrigation port 2108 comprises a blue colored band. Blue may be an advantageous color to use, as it may indicate fresh saline, which may be a common fluid transferred through the inflow port. In some embodiments, the drainage port 2106 may comprise a yellow band. The color yellow may be used, for example, to indicate urine. In some embodiments, the balloon inflation port 2104 may comprise a red color. In some embodiments, the central port 2102 may comprise a blue or purple color. It should be noted that the colors given in this example are merely examples, and various other colors may be used. Further, color may not be the only feature used to increase safety and/or to make it easier to identify which port to use for which task. For example, the embodiment illustrated in FIG. 21A comprises a different type or size of port connection method for each of the four ports. Accordingly, it would be difficult to couple to the wrong port.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the inventions are susceptible to various modifications, and alternative forms, specific examples thereof have been shown in the drawings and are herein described in detail. It should be understood, however, that the inventions are not to be limited to the particular forms or methods disclosed, but to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "passing an instrument through a central lumen of a catheter" include "instructing the passing of an instrument through the central lumen of a catheter." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

What is claimed is:

1. An indwelling cystoscopy catheter, comprising:
 a proximal end, a distal end having at least one exit port, and a flexible elongate tubular body therebetween;
 an inflatable balloon near the distal end of the catheter, the balloon transformable from an unexpanded to an expanded configuration,
 wherein the balloon in its expanded configuration comprises a low profile oblong shape suitable for anchoring within a human bladder, the low profile oblong shape comprising a first dimension in a radial direction that is at least about 1.5× of a second dimension in an axial direction, and
 wherein the balloon is sized and positioned sufficiently close to a distal tip of the distal end of the catheter to enable a cystoscope protruding from the distal tip to view ureter openings of the bladder, the balloon positioned such that an axial length from a distal end of the balloon in its expanded configuration to the distal tip of the distal end of the catheter is no greater than ⅕ of an axial length from a proximal end of the balloon in its expanded configuration to the distal tip of the distal end of the catheter;
 a first proximal port for fluid inflow;
 a second proximal port for fluid outflow;
 a third proximal port for balloon inflation, in fluid connection with the balloon; and
 a fourth proximal port for insertion of a cystoscope therethrough, the fourth proximal port aligned coaxially with the flexible elongate tubular body, the fourth proximal port including a sealing member therein, the sealing member configured to seal against an outer shaft surface of the cystoscope to prevent proximal backflow of fluid when the cystoscope is inserted therethrough, the sealing member further configured to self-seal to prevent proximal backflow of fluid when the cystoscope is not inserted therethrough,
 wherein the first, second, and fourth proximal ports are fluidly connected to a common central lumen extending through the elongate tubular body to the exit port on the distal end of the catheter.

2. The catheter of claim 1, wherein the first proximal port comprises a multifunction connector, the multifunction connector comprising a threaded portion, a tapered portion, and an annular region therebetween, wherein the annular region comprises a smaller outer diameter than the threaded portion.

3. The catheter of claim 2, further comprising a tethered cap comprising threads to couple with the threaded portion of the multifunction connector.

4. The catheter of claim 1, further comprising a tethered cap configured to seal the second proximal port.

5. The catheter of claim 4, wherein the tethered cap is integrally molded to the catheter.

6. The catheter of claim 4, further comprising a clamp that provides an alternative method of sealing the second proximal port, the clamp configured to pinch a section of tubing to limit fluid communication between the second proximal port and the common central lumen.

7. The catheter of claim 1, further comprising a tapered portion extending about the fourth proximal port.

8. The catheter of claim 1, wherein the elongate tubular body comprises a plurality of markings regularly-spaced in an axial direction.

9. The catheter of claim 1, wherein the distal tip of the distal end of the catheter extends in an axial direction no more than 1 millimeter beyond the distal end of the balloon in its expanded configuration.

10. The catheter of claim 1, wherein the distal tip of the distal end of the catheter extends in an axial direction no more than 5 millimeters beyond the distal end of the balloon in its expanded configuration.

11. The catheter of claim 1, wherein the distal tip of the distal end of the catheter extends in an axial direction no more than 10 millimeters beyond the distal end of the balloon in its expanded configuration.

12. The catheter of claim 1, wherein an expanded axial length of the balloon is no greater than about 25 millimeters.

13. The catheter of claim 1, wherein the balloon in its expanded configuration has a volume of no more than about 5 cc.

14. The catheter of claim 1, wherein the balloon in its expanded configuration has a volume of no more than about 3 cc.

15. The catheter of claim 1, wherein the distal end comprises a rounded distal tip.

16. The catheter of claim 1, wherein the distal end comprises an end cap having a slot therein.

17. The catheter of claim 1, wherein the distal end comprises at least two distal ports, wherein at least one distal port is positioned on a distal surface of the distal end and at least one distal port is positioned on a side surface of the distal end.

18. The catheter of claim 1, wherein the first proximal port is disposed at an end of a first flexible tubular member extending from the flexible elongate tubular body, the second proximal port is disposed at an end of a second flexible tubular member extending from the flexible elongate tubular body, the third proximal port is disposed at an end of a third flexible tubular member extending from the flexible elongate tubular body.

19. The catheter of claim 1, wherein the distal tip of the distal end of the catheter comprises an external bevel shape having an increasing axial length from a medial to lateral direction.

20. The catheter of claim 1, wherein the balloon is positioned such that the axial length from the distal end of the balloon in its expanded configuration to the distal tip of the distal end of the catheter is no greater than $\frac{1}{10}$ of the axial length from the proximal end of the balloon in its expanded configuration to the distal tip of the distal end of the catheter.

* * * * *

UNITED STATES PATENT AND TRADEMARK OFFICE
CERTIFICATE OF CORRECTION

PATENT NO. : 9,149,176 B2  
APPLICATION NO. : 14/542220  
DATED : October 6, 2015  
INVENTOR(S) : James Adam Greenberg et al.

Page 1 of 1

It is certified that error appears in the above-identified patent and that said Letters Patent is hereby corrected as shown below:

TITLE PAGE

In column 2 (page 1, item 56) at line 11, Under Other Publications, change "Baloon" to --Balloon--.

IN THE SPECIFICATION

In column 9 at line 20, Change "and or" to --and/or--.

In column 11 at line 45, After "Port-Selecting" insert --Valve--.

In column 12 at lines 31-32, Change "cystocope." to --cystoscope.--.

Signed and Sealed this
Fifth Day of July, 2016

Michelle K. Lee
*Director of the United States Patent and Trademark Office*